US006891083B1

(12) United States Patent
Famodu et al.

(10) Patent No.: US 6,891,083 B1
(45) Date of Patent: May 10, 2005

(54) PLANT AMINOACYL-TRNA SYNTHETASES

(76) Inventors: Omolayo O. Famodu, 216 Barrett Run Place, Newark, DE (US) 19702; Carl Simmons, 4228 Holland Dr., Des Moines, IA (US) 50310

( * ) Notice: Subject to any disclaimer, the term of this patent is extended or adjusted under 35 U.S.C. 154(b) by 0 days.

(21) Appl. No.: 09/831,683

(22) PCT Filed: Nov. 9, 1999

(86) PCT No.: PCT/US99/26478

§ 371 (c)(1),
(2), (4) Date: May 10, 2001

(87) PCT Pub. No.: WO00/28057

PCT Pub. Date: May 18, 2000

Related U.S. Application Data

(60) Provisional application No. 60/107,789, filed on Nov. 10, 1998.

(51) Int. Cl.[7] .......................... A01H 1/00; C07H 21/04; C07K 14/415; C12N 5/14; C12N 9/00
(52) U.S. Cl. .......................... 800/295; 435/6; 435/69.1; 435/468; 435/419; 435/252.3; 435/320.1; 530/370; 536/23.6; 800/278
(58) Field of Search .......................... 435/6, 69.1, 468, 435/419, 252.3, 320.1; 530/370; 536/23.6; 800/278, 295

(56) References Cited

FOREIGN PATENT DOCUMENTS

| EP | 0 785 261 A1 | 7/1997 |
|---|---|---|
| EP | 0 835 936 A2 | 4/1998 |
| WO | 97 38718 A1 | 10/1997 |

OTHER PUBLICATIONS

Day et al, Biochimica et Biophysica Acta, vol. 1399, pp. 219–224, 1998.
EMBL Sequence Data Library Accession No. D23310. Dec. 2, 1993. T Sasaki et al. Rice cDNA from callus.
EMBL Sequence Data Library Accession No. D16052. May 17, 1993. T Sasaki et al. Rice cDNA from callus.
EMBL Sequence Data Library Accession No. X83523. Dec. 21, 1994. R V Andersen.
EMBL Sequence Data Library Accession No. C27100. Aug. 6, 1997. T. Sasaki et al. Rice cDNA from callus.
EMBL Sequence Data Library Accession No. X83524. Dec. 21, 1994. R V Andersen.
Kathleen I Racher et al J Biol. Chem. vol. 266(26) 17158–17164. 1991. Expression and characterization of a recombinant yeast isoleucyl–tRNA synthetase.
EMBL Sequence Data Library Accession No. AI795505. Jul. 4, 1999. V Walbot. Maize ESTs from various cDNA libraries, sequenced at Stanford University.
EMBL Sequence Data Library Accession No. AI667809. May 17, 1999. V Walbot. Maize ESTs from various cDNA libraries sequenced at Stanford University.

EMBL Sequence Data Library Accession No. AQ574177. Jun. 3, 1999. R A Wing et al. A BAC end sequencing framework to sequence the rice genome.
EMBL Sequence Data Library Accession No. AI899999. Jul. 28, 1999 R Shoemaker et al., Public soybean EST project.
EMBL Sequence Data Library Accession No. Z98760 Nov. 16, 1997 I D Small et al Duplicated arginyl–tRNA synthetase genes in *Arabidopsis thaliana*.
EMBL Sequence Data Library Accession No. Z98759 Nov. 18, 1997. I D Small et al. Duplicated arginyl–tRNA synthetase genes in *Arabicopsis thaliana*.
Derwent Publications. Ltd AN94:134720. 1994. A. Joachimiak et al.
A Joachimiak et al., J. Chromatography, vol. 206:600–605. 1981. Heparin–sepharose col. chromatography as a new method for the purification of aminoacyl–tRNA synthetases.
Derwent Publications. Ltd., AN 1981–72059433. A. Joachimiak et al., Method for isolation of aminoacyl transfer RNA synthetases EC 6.1.1.–from plants purification and some properties of methionyl phenyl alanyl and arginyl transfer RNA synthetases from yellow lupine lupinus–luteus seeds.
A. Joachimiak et al., Int. J. of Biological Macromolecules. vol. 3(2)121–128. 1981. Method for isolation of aminoacyl–tRNA synthetases from plants purification and some properties of methionyl. phenylalanyl and arginyl tRNA synthetases from yellow lupin seeds.
EMBL Sequence Data Library Accession No. AF067773. Aug. 21, 1998. I S Day et al. Cloning of the cDNA for glutamyl–tRNA synthetase from *Arabidopsis thaliana*.
Irene S Day et al. Biochimica et Biophysica Acta vol. 1399:219–224. 1998. Cloning of the cDNA for glutamyl–tRNA synthetase from *Arabidopsis thaliana*.
EMBL Sequence Data Library Accession No. Z85984 Feb. 13, 1997 K Akashi et al., A cDNA clone encoding rice histidyl tRNA synthetase.
Kinya Akashi et al., Plant Phys. vol. 1(13) 1464. PGR97–062. A cDNA clone encoding rice histidyl–tRNA synthetase.
Kinya Akashi et al., FEBS Lett. vol. 431 39–44. 1998. Potential dual targeting of an *Arabidopsis* archaebacterial–like histidyl–tRNA synthetase to mitochondria and chloroplasts.

(Continued)

*Primary Examiner*—Phuong T. Bui
(74) *Attorney, Agent, or Firm*—Morgan & Finnegan, L.L.P.

(57) ABSTRACT

This invention relates to an isolated nucleic acid fragment encoding an aminoacyl-tRNA synthetase. The invention also relates to the construction of a chimeric gene encoding all or a portion of the aminoacyl-tRNA synthetase, in sense or antisense orientation, wherein expression of the chimeric gene results in production of altered levels of the aminoacyl-tRNA synthetase in a transformed host cell.

11 Claims, No Drawings

OTHER PUBLICATIONS

Frederick C Neidhart et al., Annu Rev Microbiology vol. 29 215–250 1975 Function and regulation of aminoacyl–tRNA synthetases in prokaryotic and eukaryotic cells.

Gilbert Eriani et al. Nature vol. 347 203–206. 1990 Partition of tRNA synthetases into two classes based on mutally exclusive sets of sequence motifs.

Adrian J. Lloyd et al., Nucleic Acids Rev. vol. 23(15):2862–2892. 1995. A broadly applicable continuous spectrophotometric assay for measuring aminoacyl–tRNA synthetase activity.

National Center for Biotechnology Information General Identifier No. 2632105. Nov. 13, 1997. I D. Small et al., Duplicated arginyl–tRNA synthetase genes in *Arabidopsis thaliana*.

National Center for Biotechnology Information General Identifier No. 3435196. Sep. 21, 1998. I. S. Day et al. Cloning of the cDNA for glutamyl–tRNA synthetase from *Arabidopsis thaliana*.

National Center for Biotechnology Information General Identifier No. 2500980. Nov. 1, 1997 R V. Andersen.

National Center for Biotechnology Information General Identifier No. 2500981 Nov. 1, 1997 R V Andersen.

National Center for Biotechnology Information General Identifier No. 2507428. Nov. 1, 1997. A A Tzagoloff et al.

National Center for Biotechnology Information General Identifier No. 3915070. Dec. 15, 1998. K Akashi et al A cDNA clone encoding rice histidyl–tRNA synthetase.

National Center for Biotechnology Information General Identifier No. 3659909. Sep. 28, 1998. K Akashi et al., Potential dual targeting of an *Arabidopsis* archaebacterial–like histidyl–tRNA synthetase to mitochondria and chloroplasts.

PLANT AMINOACYL-TRNA SYNTHETASES

This application claims the benefit of U.S. Provisional Application No. 60/107,789, filed Nov. 10, 1998.

FIELD OF THE INVENTION

This invention is in the field of plant molecular biology. More specifically, this invention pertains to nucleic acid fragments encoding aminoacyl-tRNA synthetases in plants and seeds.

BACKGROUND OF THE INVENTION

Aminoacyl-tRNA Synthetases (AARS) are enzymes that charge (acylate) tRNAs with amino acids. These charged aminoacyl tRNAs then participate in mRNA translation and protein synthesis. The AARS show high specificity for charging a specific tRNA with the appropriate amino acid, for example valyl-tRNA with valine by valyl-tRNA synthetase or tryptophanyl-tRNA with tryptophan by tryptophanyl-tRNA synthetase. In general, per organism there are at least one AARS for each of the twenty amino acids. There are exceptions however. AARS are ancient enzymes, having functioned in translation since early life evolution. Some have speculated that the earliest aminoacyl-tRNA synthetases were mRNAs, not proteins, with the proteinaceous AARS described here emerging later (Neidhardt et al., (1975) *Annu. Rev. Microbiol.* 29:215–250). AARS are structurally diverse, although AARSs for some amino acids are more closely related than for others. AARSs are generally divided into two classes, class I and class II based on structural similarity and amino acid preferences (Eriani et al., (1990) *Nature* 347:203–206).

Plants like all other cellular organisms have aminoacyl-tRNA synthetases. However, a full description of the plant 'complement' of aminoacyl-tRNA synthetases has not yet been described. Full-length cDNA, genomic clones, and EST sequences for a variety of plant aminoacyl-tRNA synthetases are known. However, several anticipated aminoacyl-tRNA synthetases have not been discovered.

Because of the central role of protein synthesis in life, any agent that inhibits or disrupts this activity is likely to be toxic. Aminoacyl-tRNA synthetases play a critical role in protein translation by linking genetic nucleic acid information to protein synthesis. Aminoacyl-tRNA synthetases perform this role by "reading" the identity of the different tRNAs and acylating them with the correct cognate amino acid. A large volume of research over several decades has been focused on identifying inhibitors of this process. Inhibitors of aminoacyl-tRNA synthetases have been found to be cytotoxic due to their inhibition of protein synthesis. As such they therefore could be used as herbicides or in aminoacyl-tRNA synthetase selectable marker systems (Lloyd et al., (1995) Nucleic Acid Research 23(15) :2882–2892). The genes disclosed herein can serve as the basis for testing whether the encoded aminoacyl-tRNA synthetases are sensitive to known inhibitors or other chemicals.

Biochemical processes are often compartmentalized in regions of cells, such as mitochondria, plastids, and lysosomes. These organelles are key sites for many biochemical pathways. Bioengineering of these processes may require targeting protein products to specific organells. One method to accomplish this involves the addition of an N-terminal prosequence (transit peptide) that directs protein entry into a specific organelle(s). Upon or shortly after transport into the organelle the transit peptide is usually proteolytically removed, and the mature protein is then able to function.

A few plant transit peptides have been shown empirically to be capable of directing fused proteins into specific organelles. However this ability appears to depend upon the structure of the protein being imported and to date it is impossible to predict whether a protein will be imported into an organelle with a given transit peptide. As such, it is advantageous to have a diversity of potential transit peptides from which the most efficient candidate can be chosen to target a protein of interest to an organelle. A number of plant transit peptides are known which direct mature proteins to mitochondria or chloroplast organells. These transit peptides are diverse in structure (length and amino acid sequence) and there is no strong consensus sequence identifying them. In addition, there is no obvious clear relationship between chloroplast targeting and mitochondrial targeting transit sequences. This invention describes a number of chloroplast-targeting and mitochondria-targeting transit peptides for (maize) aminoacyl-tRNA synthetases. These sequences will find utility in directing both aminoacyl-tRNA synthetase and other proteins into these organelles.

Accordingly, the availability of nucleic acid sequences encoding all or a portion of these enzymes would facilitate studies to better understand protein synthesis in plants, provide genetic tools for the manipulation of gene expression, protein targeting to specific organells and provide possible targets for herbicides.

SUMMARY OF THE INVENTION

The present invention relates to isolated polynucleotides comprising a nucleotide sequence encoding a polypeptide of at least 240 amino acids that has at least 80% identity based on the Clustal method of alignment when compared to a polypeptide selected from the group consisting of a corn arginyl-tRNA synthetase polypeptide of SEQ ID NO:2, a rice arginyl-tRNA synthetase polypeptide of SEQ ID NO:4, a soybean arginyl-tRNA synthetase polypeptide of SEQ ID NO:6, a wheat arginyl-tRNA synthetase polypeptide of SEQ ID NO:8. The present invention also relates to an isolated polynucleotide comprising the complement of the nucleotide sequences described above.

The present invention also relates to isolated polynucleotides comprising a nucleotide sequence encoding a polypeptide of at least 205 amino acids that has at least 90% identity based on the Clustal method of alignment when compared to a polypeptide selected from the group consisting of a corn glutamyl-tRNA synthetase polypeptide of SEQ ID NO:10, a rice glutamyl-tRNA synthetase polypeptide of SEQ ID NO:12, a soybean glutamyl-tRNA synthetase polypeptide of SEQ ID NO:14. The present invention also relates to an isolated polynucleotide comprising the complement of the nucleotide sequences described above.

The present invention also relates to isolated polynucleotides comprising a nucleotide sequence encoding a polypeptide of at least 79 amino acids that has at least 80% identity based on the Clustal method of alignment when compared to a polypeptide selected from the group consisting of a wheat glutamyl-tRNA synthetase polypeptide of SEQ ID NO:16. The present invention also relates to an isolated polynucleotide comprising the complement of the nucleotide sequences described above.

The present invention further relates to isolated polynucleotides comprising a nucleotide sequence encoding a polypeptide of at least 243 amino acids that has at least 90% identity based on the Clustal method of alignment when compared to a polypeptide selected from the group consisting of a corn histidyl-tRNA synthetase polypeptide of SEQ ID NO:18, a soybean histidyl-tRNA synthetase polypeptide of SEQ ID NO:20, a wheat histidyl-tRNA synthetase polypeptide of SEQ ID NO:22. The present invention also relates to an isolated polynucleotide comprising the complement of the nucleotide sequences described above.

The present invention relates to isolated polynucleotides comprising a nucleotide sequence encoding a polypeptide of at least 30 amino acids that has at least 60% identity based on the Clustal method of alignment when compared to a polypeptide selected from the group consisting of SEQ ID NOs:24, 26, 28, 30, 32, 34, 36 and 38.

It is preferred that the isolated polynucleotides of the claimed invention consists of a nucleic acid sequence selected from the group consisting of SEQ ID NOs: 1, 3, 5, 7, 9, 11, 13, 15, 17, 19, 21, 23, 25, 27, 29, 31, 33, 35 and 37 that codes for the polypeptide selected from the group consisting of SEQ ID NOs:2, 4, 6, 8, 10, 12, 14, 16, 18, 20, 22, 24, 26, 28, 30, 32, 34, 36 and 38. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences.

The present invention relates to a chimeric gene comprising an isolated polynucleotide of the present invention operably linked to suitable regulatory sequences.

The present invention also relates to the identification of transit peptides associated with aminoacyl-tRNA synthetases of the instant invention and the use of those transit peptides to target aminoacyl-tRNA synthetases and other operably linked proteins to specific organelles within plant cells. Transit peptide amino acid sequences are located just upstream of the mature aminoacyl-tRNA synthetase polypeptide sequences disclosed in the instant invention.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to an arginyl-tRNA synthetase polypeptide of at least 240 amino acids comprising at least 80% homology based on the Clustal method of alignment compared to a polypeptide selected from the group consisting of SEQ ID NOs:2, 4, 6, and 8.

The present invention relates to a glutamyl-tRNA synthetase polypeptide of at least 205 amino acids comprising at least 90% homology based on the Clustal method of alignment compared to a polypeptide selected from the group consisting of SEQ ID NOs:10, 12, 14 and 16.

The present invention relates to a glutamyl-tRNA synthetase polypeptide of at least 79 amino acids comprising at least 80% homology based on the Clustal method of alignment compared to a polypeptide of SEQ ID NO:16.

The present invention relates to a histidyl-tRNA synthetase polypeptide of at least 243 amino acids comprising at least 90% homology based on the Clustal method of alignment compared to a polypeptide selected from the group consisting of SEQ ID NOs:18, 20 and 22.

The present invention relates to a method of selecting an isolated polynucleotide that affects the level of expression of an arginyl-tRNA synthetase, glutamyl-tRNA synthetase or histidyl-tRNA synthetase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level an arginyl-tRNA synthetase, glutamyl-tRNA synthetase or histidyl-tRNA synthetase polypeptide in the host cell containing the isolated polynucleotide; and comparing the level of an arginyl-tRNA synthetase, glutamyl-tRNA synthetase or histidyl-tRNA synthetase polypeptide in the host cell containing the isolated polynucleotide with the level of an arginyl-tRNA synthetase, glutamyl-tRNA synthetase or histidyl-tRNA synthetase polypeptide in a host cell that does not contain the isolated polynucleotide.

Thr present invention relates to a method of obtaining a nucleic acid fragment encoding a substantial portion of an arginyl-tRNA synthetase, glutamyl-tRNA synthetase or histidyl-tRNA synthetase polypeptide gene, preferably a plant arginyl-tRNA synthetase, glutamyl-tRNA synthetase or histidyl-tRNA synthetase polypeptide gene, comprising the steps of: synthesizing an oligonucleotide primer comprising a nucleotide sequence of at least one of 60 (preferably at least one of 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences; and amplifying a nucleic acid fragment (preferably a cDNA inserted in a cloning vector) using the oligonucleotide primer. The amplified nucleic acid fragment preferably will encode a portion of an arginyl-tRNA synthetase, glutamyl-tRNA synthetase or histidyl-tRNA synthetase amino acid sequence.

The present invention also relates to a method of obtaining a nucleic acid fragment encoding all or a substantial portion of the amino acid sequence encoding an arginyl-tRNA synthetase, glutamyl-tRNA synthetase or histidyl-tRNA synthetase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of an arginyl-tRNA synthetase, glutamyl-tRNA synthetase or histidyl-tRNA synthetase, the method comprising the steps of: (a) transforming a host cell with a chimeric gene comprising a nucleic acid fragment encoding an arginyl-tRNA synthetase, glutamyl-tRNA synthetase or histidyl-tRNA synthetase, operably linked to suitable regulatory sequences; (b) growing the transformed host cell under conditions that are suitable for expression of the chimeric gene wherein expression of the chimeric gene results in production of arginyl-tRNA synthetase, glutamyl-tRNA synthetase or histidyl-tRNA synthetase in the transformed host cell; (c) optionally purifying the arginyl-tRNA synthetase, glutamyl-tRNA synthetase or histidyl-tRNA synthetase expressed by the transformed host cell; (d) treating the arginyl-tRNA synthetase, glutamyl-tRNA synthetase or histidyl-tRNA synthetase with a compound to be tested; and (e) comparing the activity of the arginyl-tRNA synthetase, glutamyl-tRNA synthetase or histidyl-tRNA synthetase that has been treated with a test compound to the activity of an untreated arginyl-tRNA synthetase, glutamyl-tRNA synthetase or histidyl-tRNA synthetase, thereby selecting compounds with potential for inhibitory activity.

The present invention relates to a composition comprising an isolated polynucleotide of the present invention.

The present invention relates to a composition comprising a polypeptide of the present invention.

The present invention relates to an isolated polynucleotide comprising the nucleotide sequence comprising at least one of 30 contiguous nucleotides of nucleic acid sequences selected from the group consisting of SEQ ID NOs:1, 3, 5, 7, 9, 11, 13, 15, 17, 19, 21, 23, 25, 27, 29, 31, 33, 35, 37 and the complement of such sequences.

The present invention relates to an expression cassette comprising an isolated polynucleotide of the present invention operably linked to a promoter.

The present invention relates to a method for positive selection of a transformed cell comprising:

(a) transforming a plant cell with an expression cassette of the present invention;

(b) growing the transformed plant cell under conditions allowing expression of the polynucleotide in an amount sufficient to complement an amino-acyl t-RNA synthesis auxotroph in a plant cell to provide a positive selection means.

The present invention relates to a method for positive selection of a transformed cell comprising:

(a) transforming a plant cell with a chimeric gene of the present invention; and (b) growing the transformed plant cell, wherein the plant cell is a monocot or a dicot and includes corn, rice, soybean or wheat under conditions allowing expression of the polynucleotide in an amount sufficient to complement an amino-acyl t-RNA synthesis.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:1, 3, 5, 7, 9, 11, 13, 15, 17, 19 and 21 and amino acid sequences SEQ ID NOs:2, 4, 6, 8, 10, 12, 14, 16, 18, 20 and 22 were determined by further sequence analysis of cDNA clones encoding the amino acid sequences set forth in SEQ ID NOs:24, 26, 28, 30, 32, 34, 36 and 38. Nucleotide SEQ ID NOs:23, 25, 27, 29, 31, 33, 35 and 37 and amino acid SEQ ID NOs:24, 26, 28, 30, 32, 34, 36 and 38 were presented in a U.S. Provisional Application No. 60/107,789, filed Nov. 10, 1998.

The sequence descriptions and Sequence Listing attached hereto comply with the rules governing nucleotide and/or amino acid sequence disclosures in patent applications as set forth in 37 C.F.R. §1.821–1.825.

TABLE 1

Aminoacyl-tRNA Synthetases

| Protein | Clone Designation | SEQ ID NO: (Nucleotide) | SEQ ID NO: (Amino Acid) |
|---|---|---|---|
| Arginyl-tRNA Synthetase | cpc1c.pk001.d11 (FIS) | 1 | 2 |
| Arginyl-tRNA Synthetase | rl0n.pk086.p16 (FIS) | 3 | 4 |
| Arginyl-tRNA Synthetase | ssm.pk0026.b10 (FIS) | 5 | 6 |
| Arginyl-tRNA Synthetase | wlk1.pk0007.f5 (FIS) | 7 | 8 |
| Glutamyl-tRNA Synthetase | p0010.cbpcp10r (CGS) | 9 | 10 |
| Glutamyl-tRNA Synthetase | rlr2.pk0032.f2 (CGS) | 11 | 12 |
| Glutamyl-tRNA Synthetase | Contig Composed of: sdc5c.pk0002.e11 sgs1c.pk001.k12 sgs1c.pk004.e20 | 13 | 14 |
| Glutamyl-tRNA Synthetase | wlm96.pk055.g5 (EST) | 15 | 16 |
| Histidyl-tRNA Synthetase | p0102.cerbb73r (CGS) | 17 | 18 |
| Histidyl-tRNA Synthetase | Contig composed of: sdp4c.pk007.c7 ssm.pk0012.d9 | 19 | 20 |
| Histidyl-tRNA Synthetase | wr1.pk0079.d1 (FIS) | 21 | 22 |
| Arginyl-tRNA Synthetase | cpc1c.pk001.d11 (EST) | 23 | 24 |
| Arginyl-tRNA Synthetase | rl0n.pk086.p16 (EST) | 25 | 26 |
| Arginyl-tRNA Synthetase | ssm.pk0026.b10 (EST) | 27 | 28 |
| Arginyl-tRNA Synthetase | wlk1.pk0007.f5 (EST) | 29 | 30 |
| Glutamyl-tRNA Synthetase | rlr2.pk0032.f2 (EST) | 31 | 32 |
| Glutamyl-tRNA Synthetase | sgs1c.pk004.e20 (EST) | 33 | 34 |
| Histidyl-tRNA Synthetase | ssm.pk0012.d9 (EST) | 35 | 36 |
| Histidyl-tRNA Synthetase | wr1.pk0079.d1 (EST) | 37 | 38 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, 15, 17, 19, 21, 23, 25, 27, 29, 31, 33, 35, 37 and the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences may be used in methods of selecting an isolated polynucleotide that affects the expression of a polypeptide in a plant cell. A method of selecting an isolated polynucleotide that affects the level of expression of a polypeptide (such as aminoacyl-tRNA synthetase) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several aminoacyl-tRNA synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other arginyl-tRNA synthetase, glutamyl-tRNA synthetase or histidyl-tRNA synthetase polypeptides, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as arginyl-tRNA synthetase, glutamyl-tRNA synthetase or histidyl-tRNA synthetase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aminoacyl-tRNA synthetase. An example of a vector for high level expression of the instant polypeptides in a bacterial host is provided (Example 8).

Additionally, the instant polypeptides can be used as a targets to facilitate design and/or identification of inhibitors of those enzymes that may be useful as herbicides. This is desirable because the polypeptides described herein catalyze various steps in aminoacyl-tRNA biosynthesis. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Composition of cDNA Libraries: Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cpc1c | Corn pooled BMS treated with chemicals related to cGMP** | cpc1c.pk001.d11 |
| p0010 | Corn log phase suspension cells treated with A23187 ® to induce mass apoptosis**** | p0010.cbpcp10r |
| p0102 | Corn early meiosis tassels* | p0102.cerbb73r |
| rl0n | Rice 15 day old leaf* | rl0n.pk086.p16 |
| rlr2 | Rice leaf 15 days after germination, 2 hours after infection of strain *Magaporthe grisea* 4360-R-62 (AVR2-YAMO) | rlr2.pk0032.f2 |
| sdc5c | | sdc5c.pk0002.e11 |
| sdp4c | | sdp4c.pk007.c7 |
| sgs1c | Soybean seeds 4 hours after germination | sgs1c.pk001.k12 sgs1c.pk004.e20 |
| ssm | Soybean shoot meristem | ssm.pk0012.d9 ssm.pk0026.b10 |

TABLE 2-continued cDNA Libraries from Corn, Rice, Soybean and Wheat

| Library | Tissue | Clone |
|---|---|---|
| wlk1 | Wheat seedlings 1 hour after inoculation with *Erysiphe graminis f.* sp *tritici* and treatment with herbicide*** | wlk1.pk0007.f5 |
| wlm96 | Wheat Seedlings 96 hours after inoculation with *Erysiphe graminis f.* sp *tritici* | wlm96.pk055.g5 |
| wr1 | Wheat root from 7 day old seedling | wr1.pk0079.d1 |

*These libraries were normalized essentially as described in U.S. Pat. No. 5,482,845, incorporated herein by reference.
**Corn tissues were individually treated with one of the following then pooled; Suramin, MAS7, dipyryridamole, zaprinast, 8-bromo-cGMPtrequinsin HCL, Compound 48/80 all of which are commercially available from Calbiochem-Noavbiochem Corp.
***Application of 6-iodo-2-propoxy-3-propyl-4(3H)-quinazolinone; synthesis and methods of using this compound are described in USSN 08/545, 827, incorporated herein by reference.
****A23187 ® is commercially available from several vendors including Calbiochem cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

Identification of cDNA Clones cDNA clones encoding aminoacyl-tRNA synthetases were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

EXAMPLE 3

Characterization of cDNA Clones Encoding Arginyl-tRNA Synthetase

The BLASTX search using the EST sequences from clones listed in Table 3 revealed similarity of the polypeptides encoded by the cDNAs to arginyl-tRNA synthetase from *Arabidopsis thaliana* (NCBI Identifier No. gi 2632105). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Arabidopsis thaliana* Arginyl-tRNA Synthetase

| Clone | Status | BLAST pLog Score to gi 2632105 |
|---|---|---|
| cpc1c.pk001.d11 | (FIS) | 146.00 |
| rl0n.pk086.p16 | (FIS) | >254.00 |
| ssm.pk0026.b10 | (FIS) | 129.00 |
| wlk1.pk0007.f5 | (FIS) | 102.00 |

The data in Table 4 represents a calculation of the percent identity of the amino acid sequences set forth in SEQ ID NOs:2, 4, 6 and 8 and the *Arabidopsis thaliana* sequence.

TABLE 4

Percent Identity of Amino Acid Sequences Deduced From the Nucleotide Sequences of cDNA Clones Encoding Polypeptides Homologous to *Arabidopsis thaliana* Arginyl-tRNA Synthetase

| SEQ ID NO. | Percent Identity to gi 2632105 |
|---|---|
| 2 | 75% |
| 4 | 66% |
| 6 | 74% |
| 8 | 73% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a arginyl-tRNA synthetase. These sequences represent the first corn, rice, soybean and wheat sequences encoding arginyl-tRNA synthetase.

EXAMPLE 4

Characterization of cDNA Clones Encoding Glutamyl-tRNA Synthetase

The BLASTX search using the EST sequences from clones listed in Table 5 revealed similarity of the polypeptides encoded by the cDNAs to glutamyl-tRNA synthetase from *Arabidopsis thaliana* (NCBI Identifier No. gi 3435196), *Hordum vulgare* (NCBI Identifier No. gi 2500980), *Nicotina tabacum* (NCBI Identifier No. gi 2500981) and *Saccharomyces cerevisiae* (NCBI Identifier No. gi 2507428). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to *Arabidopsis thaliana*, *Hordum vulgare*, *Nicotina tabacum* and *Saccharomyces cerevisiae* Glutamyl-tRNA Synthetase

| Clone | Status | BLAST pLog Score |
|---|---|---|
| p0010.cbpcp10r | (CGS) | >254.00 (gi 3435196) |
| rlr2.pk0032.f2 | (CGS) | >254.00 (gi 2500980) |
| Contig composed of:<br>sdc5c.pk0002.e11<br>sgs1c.pk001.k12<br>sgs1c.pk004.e20 | Contig | 97.40 (gi 2500981) |
| wlm96.pk055.g5 | (EST) | 18.30 (gi 2507428) |

The data in Table 6 represents a calculation of the percent identity of the amino acid sequences set forth in SEQ ID NOs:10, 12, 14 and 16 and the *Arabidopsis thaliana*, *Hordum vulgare*, *Nicotina tabacum* and *Saccharomyces cerevisiae* sequences.

TABLE 6

Percent Identity of Amino Acid Sequences Deduced From the Nucleotide Sequences Of cDNA Clones Encoding Polypeptides Homologous to *Arabidopsis thaliana*, *Hordum vulgare*, *Nicotina tabacum* and *Saccharomyces cerevisiae* Glutamyl-tRNA Synthetase

| SEQ ID NO. | Percent Identity to |
|---|---|
| 10 | 67% (gi 3435196) |
| 12 | 81% (gi 2500980) |
| 14 | 87% (gi 2500981) |
| 16 | 54% (gi 2507428) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a glutamyl-tRNA synthetase. These sequences represent the first corn, rice, soybean and wheat sequences encoding glutamyl-tRNA synthetase.

EXAMPLE 5

Characterization of cDNA Clones Encoding Histidyl-tRNA Synthetase

The BLASTX search using the EST sequences from clones listed in Table 7 revealed similarity of the polypeptides encoded by the cDNAs to histidyl-tRNA synthetase from *Oryza sativa* (NCBI Identifier No. gi 3915070) and *Arabidopsis thaliana* (NCBI Identifier No. gi 3659909). Shown in Table 7 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 7

BLAST Results for Sequences Encoding Polypeptides Homologous to *Oryza sativa* and *Arabidopsis thaliana* Histidyl-tRNA Synthetase

| Clone | Status | BLAST pLog Score |
| --- | --- | --- |
| p0102.cerbb73r | (CGS) | >254.00 (gi 3915070) |
| Contig composed of: sdp4c.pk007.c7 ssm.pk0012.d9 | Contig | 84.22 (gi 3659909) |
| wr1.pk0079.d1 | (FIS) | 98.30 (gi 3659909) |

The data in Table 8 represents a calculation of the percent identity of the amino acid sequences set forth in SEQ ID NOs:18, 20 and 22 and the *Oryza sativa* and *Arabidopsis thaliana* sequences.

TABLE 8

Percent Identity of Amino Acid Sequences Deduced From the Nucleotide Sequences of cDNA Clones Encoding Polypeptides Homologous to *Oryza sativa* and *Arabidopsis thaliana* Histidyl-tRNA Synthetase

| SEQ ID NO. | Percent Identity to |
| --- | --- |
| 18 | 87% |
| 20 | 67% |
| 22 | 67% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a histidyl-tRNA synthetase. These sequences represent the first corn, soybean and wheat sequences encoding histidyl-tRNA synthetase.

EXAMPLE 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pal gene in p35S/Ac is under the control of the $^{35}$S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μL in diameter) are coated with DNA using the following technique. Ten fig of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 7

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

EXAMPLE 9

Evaluating Compounds for Their Ability to Inhibit the Activity of Aminoacyl-tRNA Synthetases The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme.

For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for aminoacyl-tRNA synthetase activity are presented by (Lloyd et al., (1995) Nucleic Acid Research 23(15):2882–2892).

What is claimed is:

1. An isolated polynucleotide comprising:
   (a) a nucleotide sequence encoding a polypeptide having Glutamyl-tRNA synthetase activity, wherein the polypeptide has an amino acid sequence of at least 80% sequence identity, based on the Clustal pairwise alignment method with default parameters of KTUPLE=1, GAP PENALTY=3, WINDOW=5 and DIAGONALS SAVED=5, when compared to SEQ ID NO:10, or
   (b) a full-length complement of the nucleotide sequence of (a).

2. The polynucleotide of claim 1, wherein the amino acid sequence of the polypeptide has at least 95% sequence identity, based on the Clustal pairwise alignment method with default parameters of KTUPLE=1, GAP PENALTY=3, WINDOW=5 and DIAGONALS SAVED=5, when compared to one of SEQ ID NO:10.

3. The polynucleotide of claim 1, wherein the amino acid sequence of the polypeptide comprises SEQ ID NO:10.

4. The polynucleotide of claim 1, wherein the nucleotide sequence comprises SEQ ID NO:9.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

UNITED STATES PATENT AND TRADEMARK OFFICE
CERTIFICATE OF CORRECTION

PATENT NO. : 6,891,083 B1
DATED : May 10, 2005
INVENTOR(S) : Famodu Omolayo O. and Simmons, Carl It is certified that error appears in the above-identified patent and that said Letters Patent is hereby corrected as shown below:

Column 87,
Line 45, please delete "80%" and insert therefor -- 90% --.

Signed and Sealed this

Twenty-third Day of August, 2005

JON W. DUDAS
*Director of the United States Patent and Trademark Office*

SEQUENCE LISTING

<160> NUMBER OF SEQ ID NOS: 38

<210> SEQ ID NO 1
<211> LENGTH: 1178
<212> TYPE: DNA
<213> ORGANISM: Zea mays

<400> SEQUENCE: 1

```
gcacgaggtt tctataatcc ttatattcct caagtgctgg aggaattgag taacaaaggc      60
ttgatcaagg agagtgaggg tgcccgagtt atatttattc aaggtcatca aatcccttg     120
attgttgtta agagtgatgg tggcttcaac tatgcctcaa cagacttaac tgctctttgg    180
tatcggctca atgttgagca ggcagagtgg atcatatatg ttacagatgt tggtcagcag    240
cagcactttg acatggtttt cagtgctgca aagatggccg ttggctcccc agatccaagt    300
gaaaagaagt tccgaaaac aagccatgtt ggatttggtc ttgttcttgg ttcagatggc    360
aagcggttcc gaacccgcag tactgaggtt gttcgattgg tagagctact tgatgaggct    420
aaatctcgga gcaaatcaga actactacaa cggctcactg aaaatggcaa aattgttgac    480
tggacggatg aggaattaga gcaaacttca gaggctgttg gatatggtgc tgtgaagtac    540
gctgatctaa aaataacag gctcactaat tacacattta gttttgaaca aatgctgagc    600
gataagggaa atactgctgt gtaccttcag tatgcacatg ctcgtatttg ttccattatt    660
cggaaatcca acaagaacgt ggaagagctg aagatgagtg gagccatttc tctcgaccat    720
ccggatgagc gcgtgttggg gctgtatctt atccgatttg cagaggttgt tgaagaggca    780
tgcacgaatc tacttccaaa tgttgtgtgt gaatacttgt acaatctatc tgaaatgttc    840
acaaaattct ataccaactg ccaggtggtt gggtcgccgg aggagacgag ccggttgttg    900
ctttgccagg cgactgctgt tgtcatgcga cagtgcttca acctgctcgg gatcacgcca    960
gtatacaagc tgtgattggc tgcatgttcg attaatacat tcaacatgta gaaaccccaa   1020
ttcatcatgg ttgcagtttt ggtcttgtaa cctagttgag gcagttaaca taatctactg   1080
tcctgtttga aaacagaagg aactcaaaag gttgtatcaa aatgtgcttg cagagtttct   1140
gttactaaaa aaaaaaaaaa aaaaaaaaaa aaaaaaaa                           1178
```

<210> SEQ ID NO 2
<211> LENGTH: 321
<212> TYPE: PRT
<213> ORGANISM: Zea mays

<400> SEQUENCE: 2

Phe Tyr Asn Pro Tyr Ile Pro Gln Val Leu Glu Glu Leu Ser Asn Lys
 1               5                  10                  15

Gly Leu Ile Lys Glu Ser Glu Gly Ala Arg Val Ile Phe Ile Gln Gly
            20                  25                  30

His Gln Ile Pro Leu Ile Val Val Lys Ser Asp Gly Gly Phe Asn Tyr
        35                  40                  45

Ala Ser Thr Asp Leu Thr Ala Leu Trp Tyr Arg Leu Asn Val Glu Gln
    50                  55                  60

Ala Glu Trp Ile Ile Tyr Val Thr Asp Val Gly Gln Gln Gln His Phe
65                  70                  75                  80

Asp Met Val Phe Ser Ala Ala Lys Met Ala Gly Trp Leu Pro Asp Pro
                85                  90                  95

Ser Glu Lys Lys Phe Pro Lys Thr Ser His Val Gly Phe Gly Leu Val

```
              100                 105                 110
Leu Gly Ser Asp Gly Lys Arg Phe Arg Thr Arg Ser Thr Glu Val Val
        115                 120                 125

Arg Leu Val Glu Leu Leu Asp Glu Ala Lys Ser Arg Ser Lys Ser Glu
    130                 135                 140

Leu Leu Gln Arg Leu Thr Glu Asn Gly Lys Ile Val Asp Trp Thr Asp
145                 150                 155                 160

Glu Glu Leu Glu Gln Thr Ser Glu Ala Val Gly Tyr Gly Ala Val Lys
                165                 170                 175

Tyr Ala Asp Leu Lys Asn Asn Arg Leu Thr Asn Tyr Thr Phe Ser Phe
            180                 185                 190

Glu Gln Met Leu Ser Asp Lys Gly Asn Thr Ala Val Tyr Leu Gln Tyr
        195                 200                 205

Ala His Ala Arg Ile Cys Ser Ile Ile Arg Lys Ser Asn Lys Asn Val
    210                 215                 220

Glu Glu Leu Lys Met Ser Gly Ala Ile Ser Leu Asp His Pro Asp Glu
225                 230                 235                 240

Arg Val Leu Gly Leu Tyr Leu Ile Arg Phe Ala Glu Val Val Glu Glu
                245                 250                 255

Ala Cys Thr Asn Leu Leu Pro Asn Val Val Cys Glu Tyr Leu Tyr Asn
            260                 265                 270

Leu Ser Glu Met Phe Thr Lys Phe Tyr Thr Asn Cys Gln Val Val Gly
        275                 280                 285

Ser Pro Glu Glu Thr Ser Arg Leu Leu Leu Cys Gln Ala Thr Ala Val
    290                 295                 300

Val Met Arg Gln Cys Phe Asn Leu Leu Gly Ile Thr Pro Val Tyr Lys
305                 310                 315                 320

Leu

<210> SEQ ID NO 3
<211> LENGTH: 2019
<212> TYPE: DNA
<213> ORGANISM: Oryza sativa

<400> SEQUENCE: 3
gcacgagctt acagctgaac acagtgtaca gagcgtcgag caacaactct gtacattaat    60
cacatcttcc ctgcgtgcaa cagtacctga cctggatgtg gaaccgatgc ttgaagtctc   120
aaaaccaggt tttggggatt accagtgcaa caatgctatg agtgtatttt caagaataag   180
aggatccgca acaaacttcc gtaaccccat ggcagttggg caggcaattg caaataaccct   240 cccccagtca atattatcg aatccatctc tgttgctgga cctggttaca ttaacataac   300
gttatccagc aattggattg cacagaggat acaagacatg cttgtttgtg gtatcaaaac   360
atgggcacca atcttacctg ttaagagggc agtgctggat ttttcatccc ctaatattgc   420
aaaagagatg catgttggac atataaggtc caccataatt ggagatactc tagctcacat   480
gtttgagttc acaaatgttg aagttcttcg acgtaaccat gtgggagact ggggtacaca   540
gtttgggatg ttgatagagt ttctgtttga gcaattccca gattgggagg atgttgggaa   600
ccaggctgtt ggagatcttc agagcttcta caaggcatcc aagaaaagat ttgacgatga   660
tcctgatttt aaggagaggg ctcggcaagc ggtagttcga ctgcagggag agaagataa   720 ataccgagct gcttggaaaa aaatatgtca aatcagccga atggagtttg atttggtata   780
caaacgcctt aatgtgaagc ttgaagaaaa gggagagagc ttttacaacc cctacattcc   840
```

-continued

```
acctgttttg gaggaattga ctaacaaagg tttgattgtg aaagtaaag gcgctcgagt      900
aatattcgtt gaagaccacc ctttgatagt gattaaacaa gatggcggct tcaactatgc      960
ctccacagac ttggcagctc tttggtatcg gcttaatgtg gagaaggcag aatggataat     1020
atatgtaacg gatgtaggtc agcaacgaca ctttcatatg ttgttcactg ctgcaaagat     1080
ggctggctgg ctcccagaac aaaatggaaa gaaatacccg aaagcaagcc atgttggatt     1140
tggcctagtt cttggttcag atggcaagcg cttccggact cgttgttctg aagttgttcg     1200
actggttgat ctacttgatg aggctaaagc tcggagcaaa gcacaactca tcaaacgttt     1260
cactggaaat ggtcaaattg ctgactggac agatgatgag ctcgatagga cttcagaggc     1320
tataggatat ggtgctgtta agtattcaga tcttaaaaac aatcggctga cagactacac     1380
atttagtttt gatcaaatgc tgagtgacaa gggaaatact gctgtctacc ttcagtatgc     1440
acatgcccgt atctgttcca ttatcaggaa agccagcaag gatgtagaga agttaaaaat     1500
gactggagcc attacccttg ccatccata cgagcgtttc ctcggattac atctcatcca     1560
gtttaccgag gttgtggagc aggcttgtgc cgatttacag ccccatcgtt tgtgcgacta     1620
cttgtatagc ttatccttaa cattctccaa gttttacaca aactgccagg tggttggttc     1680
acctgaagaa acgagccgtc tgctgctatg tgaagcaaca ggcatcatca tgaggcagtg     1740
tttccacctg ttgggcataa caccagtgca caagctatga caatccacgc cccaatacaa     1800
tgccatttgg aagaatttcc aagctataaa tgtaaatagt atattacctt aaaagctaat     1860
gtaaatattg agtggtggta gtgtcttgta aataggcggt ggctgtaagg cctcgccatc     1920
tctgtacatt cttcaatttt ttaatatact acggtcggcg ttctttgccg tccctacgaa     1980
aataaaaaaa aataatgtaa aaaaaaaaaa aaaaaaaa                            2019
```

<210> SEQ ID NO 4
<211> LENGTH: 587
<212> TYPE: PRT
<213> ORGANISM: Oryza sativa

<400> SEQUENCE: 4

```
Glu His Ser Val Gln Ser Val Glu Gln Gln Leu Cys Thr Leu Ile Thr
 1               5                  10                  15

Ser Ser Leu Arg Ala Thr Val Pro Asp Leu Asp Val Glu Pro Met Leu
             20                  25                  30

Glu Val Ser Lys Pro Gly Phe Gly Asp Tyr Gln Cys Asn Asn Ala Met
         35                  40                  45

Ser Val Phe Ser Arg Ile Arg Gly Ser Ala Thr Asn Phe Arg Asn Pro
     50                  55                  60

Met Ala Val Gly Gln Ala Ile Ala Asn Leu Pro Gln Ser Asn Ile
 65                  70                  75                  80

Ile Glu Ser Ile Ser Val Ala Gly Pro Gly Tyr Ile Asn Ile Thr Leu
                 85                  90                  95

Ser Ser Asn Trp Ile Ala Gln Arg Ile Gln Asp Met Leu Val Cys Gly
            100                 105                 110

Ile Lys Thr Trp Ala Pro Ile Leu Pro Val Lys Arg Ala Val Leu Asp
        115                 120                 125

Phe Ser Ser Pro Asn Ile Ala Lys Glu Met His Val Gly His Ile Arg
    130                 135                 140

Ser Thr Ile Ile Gly Asp Thr Leu Ala His Met Phe Glu Phe Thr Asn
145                 150                 155                 160

Val Glu Val Leu Arg Arg Asn His Val Gly Asp Trp Gly Thr Gln Phe
```

-continued

```
                165                 170                 175
Gly Met Leu Ile Glu Phe Leu Phe Glu Gln Phe Pro Asp Trp Glu Asp
            180                 185                 190
Val Gly Asn Gln Ala Val Gly Asp Leu Gln Ser Phe Tyr Lys Ala Ser
            195                 200                 205
Lys Lys Arg Phe Asp Asp Pro Asp Phe Lys Glu Arg Ala Arg Gln
210                 215                 220
Ala Val Val Arg Leu Gln Gly Gly Glu Asp Lys Tyr Arg Ala Ala Trp
225                 230                 235                 240
Lys Lys Ile Cys Gln Ile Ser Arg Met Glu Phe Asp Leu Val Tyr Lys
            245                 250                 255
Arg Leu Asn Val Lys Leu Glu Glu Lys Gly Glu Ser Phe Tyr Asn Pro
            260                 265                 270
Tyr Ile Pro Pro Val Leu Glu Glu Leu Thr Asn Lys Gly Leu Ile Val
            275                 280                 285
Glu Ser Lys Gly Ala Arg Val Ile Phe Val Glu Asp His Pro Leu Ile
            290                 295                 300
Val Ile Lys Gln Asp Gly Gly Phe Asn Tyr Ala Ser Thr Asp Leu Ala
305                 310                 315                 320
Ala Leu Trp Tyr Arg Leu Asn Val Glu Lys Ala Glu Trp Ile Ile Tyr
            325                 330                 335
Val Thr Asp Val Gly Gln Gln Arg His Phe His Met Leu Phe Thr Ala
            340                 345                 350
Ala Lys Met Ala Gly Trp Leu Pro Glu Gln Asn Gly Lys Lys Tyr Pro
            355                 360                 365
Lys Ala Ser His Val Gly Phe Gly Leu Val Leu Gly Ser Asp Gly Lys
            370                 375                 380
Arg Phe Arg Thr Arg Cys Ser Glu Val Val Arg Leu Val Asp Leu Leu
385                 390                 395                 400
Asp Glu Ala Lys Ala Arg Ser Lys Ala Gln Leu Ile Lys Arg Phe Thr
            405                 410                 415
Gly Asn Gly Gln Ile Ala Asp Trp Thr Asp Asp Glu Leu Asp Arg Thr
            420                 425                 430
Ser Glu Ala Ile Gly Tyr Gly Ala Val Lys Tyr Ser Asp Leu Lys Asn
            435                 440                 445
Asn Arg Leu Thr Asp Tyr Thr Phe Ser Phe Asp Gln Met Leu Ser Asp
            450                 455                 460
Lys Gly Asn Thr Ala Val Tyr Leu Gln Tyr Ala His Ala Arg Ile Cys
465                 470                 475                 480
Ser Ile Ile Arg Lys Ala Ser Lys Asp Val Glu Lys Leu Lys Met Thr
            485                 490                 495
Gly Ala Ile Thr Leu Gly His Pro Tyr Glu Arg Phe Leu Gly Leu His
            500                 505                 510
Leu Ile Gln Phe Thr Glu Val Glu Gln Ala Cys Ala Asp Leu Gln
            515                 520                 525
Pro His Arg Leu Cys Asp Tyr Leu Tyr Ser Leu Ser Leu Thr Phe Ser
            530                 535                 540
Lys Phe Tyr Thr Asn Cys Gln Val Val Gly Ser Pro Glu Glu Thr Ser
545                 550                 555                 560
Arg Leu Leu Leu Cys Glu Ala Thr Gly Ile Ile Met Arg Gln Cys Phe
            565                 570                 575
His Leu Leu Gly Ile Thr Pro Val His Lys Leu
            580                 585
```

<210> SEQ ID NO 5
<211> LENGTH: 1123
<212> TYPE: DNA
<213> ORGANISM: Glycine max

<400> SEQUENCE: 5

| | | | | | |
|---|---|---|---|---|---|
| gcacgaggtt | gagggtgtag | acataccact | tattgctgtg | aaaagagatg | gtggctacaa | 60 |
| ctattttaca | actgatctag | catcactttg | gtatcgtcta | aatgaagaaa | aacttgaatg | 120 |
| gattgtatat | gttacagata | ttgggcagca | acagcacttt | gatatgctat | ttaaggccta | 180 |
| taggcgtgca | ggttggttac | caaggatga | gaatgcgtat | ccaaaatgta | ctcatatagg | 240 |
| ttttggtctt | gttcttgggg | aagatggaaa | acgatttcgg | actcgcagca | gtgaggttgt | 300 |
| tcgattagtt | gatttacttg | atgaagctaa | aaggcgctgt | aaaattgcca | ttcttgaacg | 360 |
| tgatacaact | aaagattggt | ctgaggagga | gatcgagaaa | acatccgagg | cagttggtta | 420 |
| tggggctgtt | aagtatgctg | atttgaagat | caacagatta | caaattaca | ccttcaactt | 480 |
| tgatcagatg | cttaatgaca | agggaatac | tgctgtttat | ttgctgtatg | cacatgctag | 540 |
| gatctgttcc | attatcagga | aatctggtaa | agacatagaa | gaagtaaaga | gaaatgggaa | 600 |
| aatagtgttg | gatcatgaag | atgaacgtgc | attggggctt | catttgctac | aatttcctga | 660 |
| ggtttttgag | gaggcatgca | ccaatttgtt | gcccaatttc | ttgtgtgaat | acctttacaa | 720 |
| tttggcagaa | atctttacaa | aaaaatttta | cgctaattgt | caggttgtgg | ggtcgcctga | 780 |
| ggaaaccagt | agactcttgc | tatgtgaagc | aacggtgact | gtgatgagac | actgcttta | 840 |
| tctccttgga | attgaacatg | tatacaggct | atgacctata | tataagagat | tcatatgcaa | 900 |
| attcttcatc | agatttttt | gggatataca | agtataggaa | acttcacaat | gaaaattgtt | 960 |
| caggcaaatt | cgaccactcc | ttccctctt | ccattttgtt | aatttattt | gagttgtaac | 1020 |
| ttgtaagaag | taaagtaaat | aatttatagc | aatattgttg | acaaggtccc | atgaaaaatt | 1080 |
| tatttagatg | agttatattt | cgtttaaaaa | aaaaaaaaaa | aaa | | 1123 |

<210> SEQ ID NO 6
<211> LENGTH: 288
<212> TYPE: PRT
<213> ORGANISM: Glycine max

<400> SEQUENCE: 6

Val Glu Gly Val Asp Ile Pro Leu Ile Ala Val Lys Arg Asp Gly Gly
 1               5                  10                  15

Tyr Asn Tyr Phe Thr Thr Asp Leu Ala Ser Leu Trp Tyr Arg Leu Asn
             20                  25                  30

Glu Glu Lys Leu Glu Trp Ile Val Tyr Val Thr Asp Ile Gly Gln Gln
         35                  40                  45

Gln His Phe Asp Met Leu Phe Lys Ala Tyr Arg Arg Ala Gly Trp Leu
     50                  55                  60

Pro Lys Asp Glu Asn Ala Tyr Pro Lys Cys Thr His Ile Gly Phe Gly
 65                  70                  75                  80

Leu Val Leu Gly Glu Asp Gly Lys Arg Phe Arg Thr Arg Ser Ser Glu
                 85                  90                  95

Val Val Arg Leu Val Asp Leu Leu Asp Glu Ala Lys Arg Arg Cys Lys
            100                 105                 110

Ile Ala Ile Leu Glu Arg Asp Thr Thr Lys Asp Trp Ser Glu Glu Glu
        115                 120                 125

-continued

```
Ile Glu Lys Thr Ser Glu Ala Val Gly Tyr Gly Ala Val Lys Tyr Ala
    130                 135                 140
Asp Leu Lys Ile Asn Arg Leu Thr Asn Tyr Thr Phe Asn Phe Asp Gln
145                 150                 155                 160
Met Leu Asn Asp Lys Gly Asn Thr Ala Val Tyr Leu Leu Tyr Ala His
                165                 170                 175
Ala Arg Ile Cys Ser Ile Ile Arg Lys Ser Gly Lys Asp Ile Glu Glu
            180                 185                 190
Val Lys Arg Asn Gly Lys Ile Val Leu Asp His Glu Asp Glu Arg Ala
        195                 200                 205
Leu Gly Leu His Leu Leu Gln Phe Pro Glu Val Phe Glu Glu Ala Cys
    210                 215                 220
Thr Asn Leu Leu Pro Asn Phe Leu Cys Glu Tyr Leu Tyr Asn Leu Ala
225                 230                 235                 240
Glu Ile Phe Thr Lys Lys Phe Tyr Ala Asn Cys Gln Val Val Gly Ser
                245                 250                 255
Pro Glu Glu Thr Ser Arg Leu Leu Leu Cys Glu Ala Thr Val Thr Val
            260                 265                 270
Met Arg His Cys Phe Tyr Leu Leu Gly Ile Glu His Val Tyr Arg Leu
        275                 280                 285
```

<210> SEQ ID NO 7
<211> LENGTH: 1041
<212> TYPE: DNA
<213> ORGANISM: Triticum aestivum

<400> SEQUENCE: 7

```
gcacgagtgt ttttcaaggc tgccaggatg gctggttggc ttccagatcc aaaggaaaag      60
aagttcccaa aaacgagtca tgttgggttt ggccttgttc ttggagcaga tggcaagcgc     120
ttccgaactc gtagtactga ggttgttcgg ttgggagacc tacttgatga ggctaaatct     180
cgaagtaaat cagaacttct ccagcgtctc actgaaaatg gtaaaattgt tgactggact     240
gatgaggaac tagagcaaac ttcaaaggca gtaggatatg cgctgtcaa gtatgcggat     300
ctgaagaata accgactgac taattacacg ttcagctttg atcagatgct aagtgacaag     360
ggaaatactg ctgtctatct tcagtatgct catgctcgta tctgctccat cattcgaaaa     420
tccaacatgg atgtagaaga gctaaaagtg agtgggaaca tttctcttgc tcatccagat     480
gagcgtgtct tgggactgta tcttatccgt tatgcagaga ttgttgaaga ggcatgcacc     540
aatctccttc ccagtgttct gtgtgaatac ctatacaact tatccgaaat gttcacaagg     600
ttctacacaa actgccaggt tgttggatca ccggaggagc caagccggct gctgctttgc     660
gaagcgacgg gggtcgtcat gcgacaatgc ttccagctgc ttgggatcac accggtttac     720
atgctgtgat tggccagtgt ctgatccttc acatcataca tttgttttcca cacaagcccg     780
tctccatggt tacagttttc gtccttgtaa cctattacct ctgttctgaa atataattcg     840
ctgggggagt tcagtttaca ctcccccaaa gacatatatt taggtacgga gggagtagta     900
gttggcacca ctaacatact ctgagtcaga ttgccccatt tgagaactga agcatctggt     960
attctggttg aaactactat gtagcaaagg atagtcgaaa catgtttatt ttttgccctg    1020
tcaaaaaaaa aaaaaaaaa a                                                1041
```

<210> SEQ ID NO 8
<211> LENGTH: 240
<212> TYPE: PRT
<213> ORGANISM: Triticum aestivum

```
<400> SEQUENCE: 8

Val Phe Phe Lys Ala Ala Arg Met Ala Gly Trp Leu Pro Asp Pro Lys
 1               5                  10                  15

Glu Lys Lys Phe Pro Lys Thr Ser His Val Gly Phe Gly Leu Val Leu
             20                  25                  30

Gly Ala Asp Gly Lys Arg Phe Arg Thr Arg Ser Thr Glu Val Val Arg
         35                  40                  45

Leu Gly Asp Leu Leu Asp Glu Ala Lys Ser Arg Ser Lys Ser Glu Leu
     50                  55                  60

Leu Gln Arg Leu Thr Glu Asn Gly Lys Ile Val Asp Trp Thr Asp Glu
 65                  70                  75                  80

Glu Leu Glu Gln Thr Ser Lys Ala Val Gly Tyr Gly Ala Val Lys Tyr
                 85                  90                  95

Ala Asp Leu Lys Asn Asn Arg Leu Thr Asn Tyr Thr Phe Ser Phe Asp
            100                 105                 110

Gln Met Leu Ser Asp Lys Gly Asn Thr Ala Val Tyr Leu Gln Tyr Ala
        115                 120                 125

His Ala Arg Ile Cys Ser Ile Ile Arg Lys Ser Asn Met Asp Val Glu
    130                 135                 140

Glu Leu Lys Val Ser Gly Asn Ile Ser Leu Ala His Pro Asp Glu Arg
145                 150                 155                 160

Val Leu Gly Leu Tyr Leu Ile Arg Tyr Ala Glu Ile Val Glu Glu Ala
                165                 170                 175

Cys Thr Asn Leu Leu Pro Ser Val Leu Cys Glu Tyr Leu Tyr Asn Leu
            180                 185                 190

Ser Glu Met Phe Thr Arg Phe Tyr Thr Asn Cys Gln Val Val Gly Ser
        195                 200                 205

Pro Glu Glu Pro Ser Arg Leu Leu Cys Glu Ala Thr Gly Val Val
    210                 215                 220

Met Arg Gln Cys Phe Gln Leu Leu Gly Ile Thr Pro Val Tyr Met Leu
225                 230                 235                 240

<210> SEQ ID NO 9
<211> LENGTH: 2572
<212> TYPE: DNA
<213> ORGANISM: Zea mays

<400> SEQUENCE: 9
actagtcacc agttactttta ccaatccgcg ccggtggtaa ccctgccttt ggcggcggct     60
agccggtacc cagtgtgcgc actccctcta tctccctctt ggcgacgact gggcggccgt    120
cgctgctgcc ctacgccgtc ttcgggctct cgttgtcga cgagcgccac aaggttccta    180 ccattttaa gaaaaaaaga tcaatggagg cagctttgtc attctccaag acagcccac    240 caatttcgat aatttgtgct gcaaagcttg tgggtctacc cctaaccatc aatcatagcc    300
tcgctgctgg ctcggcaccc accctacagt ttgcttctgg agaatcactc catggtgtca    360
acccaatcat cctctacatt gctagaggtg catcaattgc ctccttatct ggaaagaatg    420
atattgagtt tgggcatgtt gttgaatggc ttgaatatgc ccccaccttc ctttcaggct    480
ctgaatttga aaatgcatgc ttatttgttg atggattctt ggcctccgg accttttctgg    540 ttggtcatgg cctgacaatt gctgacattg cagtttggtc aaatcttgct ggaattggtc    600
agcggtggga gagtctaagg aaatcaaaga aataccaaaa tcttgttcgc tggttcaaca    660
gcatagattc agaatacaaa gaggcactga acgaagttgt ggctgcattt gttgggaaac    720
```

-continued

```
gaggtattgg aaaatctcct gcacctagcc ttaaggagaa ggtacatgac tcaaaggacc    780
catcagctcc agaagttgat ctccctggtg caaaagttgg gaaagtctgc gttcgttttg    840
ccccagagcc tagtggttac ctccatattg ggcatgcaaa ggctgcacta ttgaacaaat    900
actttgctga agatatcaa ggcgcttaa tagttcgatt tgatgacaca aacccttcaa     960
aagaaagcaa tgagtttgtt gagaatcttt tgaaagatat tgagacgttg gggatcaaat   1020
atgatgctgt cacatacaca tctgattatt tcccaaagct aatggaaatg gctgagagtt   1080
tgataaagca gggtaaagca tatattgatg acacaccaaa ggagcaaatg aggaaagaga   1140
ggatggacgg tattgagtca aggtgcagaa ataataccgt ggaggaaaat ctctcattat   1200
ggaaagagat ggttaatgga actgaaaggg gcatgcagtg ctgtgtacgg ggtaaacttg   1260
acatgcagga tcctaacaag tcactcaggg atcctgttta ctaccgctgt aatactgatc   1320
cacaccatcg tgttggttcg aagtacaagg tctatccaac atatgacttt gcgtgcccat   1380
tgttgatgc attggagggg gtaacacatg ctcttcgttc cagtgaatat catgacagaa    1440
atgcacaata ttatcgaatt cttcaagaca tgggggttgag gagagtagaa atttatgagt   1500
tcagccgatt gaatatggtt tacactcttc taagcaagcg aaagcttctt tggtttgtac   1560
aaaacaagaa ggtcgaagat tggacagacc acgttttcc cactgtccaa ggcatagtac    1620
gtcgggctt gaaggttgag gcattgatac agtttatact ccaacagggt gcttcaaaaa    1680
atctgaatct catggagtgg gataaactct ggacaatcaa caagaagata attgatccag   1740
tgtgcgcaag gcatactgct gtgctaaaag accagcgtgt catcttcact cttacaaatg   1800
gtccagagga gccatttgtt cgaattttac caagacataa gaaatttgag ggtgctggaa   1860
agaaggctac aacctttgcc aacagaattt ggctcgatta tgctgatgcg gcagctatta   1920
acaagggtga ggaagtaacc cttatggatt ggggggaatgc tattgttaaa gagatcaagg   1980
tggagagtgg agtaattact gaactagttg agaactgca tcttgagggg tctgtgaaaa     2040
caacaaaatt gaagatcaca tggctagcag atatagagga gctagttccc ctttcattgg   2100
ttgaatttga ttacctcatc agcaagaaaa agctagagga agacgaggac ttcctcgaca   2160
atctcaaccc ttgcactcga cgggaaatcc cagcccttgg agatgcgaac atgaggaaca   2220
tcaagcgtgg agagatcata cagctcgaga ggaaaggcta ctataggtgt gatgcccctt   2280
ttatcagatc gtccaaaccg gtggtcctgt ttgcgatccc agatggcagg cagcaggcct   2340
cgcttagcta ggcatggtga ccaccttttg ggcacatgga attcctgagt tgacaatgag   2400
tattgttgca ttgtacactt taatattgta ctgtgattag gctttactcg cggtggatgt   2460
ctttcaccgc tagatggcca gaggcatatc ctgccaacca agcagagcag ccattttgat   2520
tttggtctat gatacttta cctgagcttg aagattccta tacttctcta gc            2572
```

<210> SEQ ID NO 10
<211> LENGTH: 715
<212> TYPE: PRT
<213> ORGANISM: Zea mays

<400> SEQUENCE: 10

```
Met Glu Ala Ala Leu Ser Phe Ser Lys Asp Ser Pro Ile Ser Ile
 1               5                  10                  15

Ile Cys Ala Ala Lys Leu Val Gly Leu Pro Leu Thr Ile Asn His Ser
                20                  25                  30

Leu Ala Ala Gly Ser Ala Pro Thr Leu Gln Phe Ala Ser Gly Glu Ser
        35                  40                  45
```

-continued

```
Leu His Gly Val Asn Pro Ile Ile Leu Tyr Ile Ala Arg Gly Ala Ser
     50                  55                  60

Ile Ala Ser Leu Ser Gly Lys Asn Asp Ile Glu Phe Gly His Val Val
 65                  70                  75                  80

Glu Trp Leu Glu Tyr Ala Pro Thr Phe Leu Ser Gly Ser Glu Phe Glu
                 85                  90                  95

Asn Ala Cys Leu Phe Val Asp Gly Phe Leu Ala Ser Arg Thr Phe Leu
            100                 105                 110

Val Gly His Gly Leu Thr Ile Ala Asp Ile Ala Val Trp Ser Asn Leu
        115                 120                 125

Ala Gly Ile Gly Gln Arg Trp Glu Ser Leu Arg Lys Ser Lys Lys Tyr
    130                 135                 140

Gln Asn Leu Val Arg Trp Phe Asn Ser Ile Asp Ser Glu Tyr Lys Glu
145                 150                 155                 160

Ala Leu Asn Glu Val Ala Ala Phe Val Gly Lys Arg Gly Ile Gly
            165                 170                 175

Lys Ser Pro Ala Pro Ser Leu Lys Glu Lys Val His Asp Ser Lys Asp
        180                 185                 190

Pro Ser Ala Pro Glu Val Asp Leu Pro Gly Ala Lys Val Gly Lys Val
    195                 200                 205

Cys Val Arg Phe Ala Pro Glu Pro Ser Gly Tyr Leu His Ile Gly His
    210                 215                 220

Ala Lys Ala Ala Leu Leu Asn Lys Tyr Phe Ala Glu Arg Tyr Gln Gly
225                 230                 235                 240

Arg Leu Ile Val Arg Phe Asp Asp Thr Asn Pro Ser Lys Glu Ser Asn
            245                 250                 255

Glu Phe Val Glu Asn Leu Leu Lys Asp Ile Glu Thr Leu Gly Ile Lys
            260                 265                 270

Tyr Asp Ala Val Thr Tyr Thr Ser Asp Tyr Phe Pro Lys Leu Met Glu
        275                 280                 285

Met Ala Glu Ser Leu Ile Lys Gln Gly Lys Ala Tyr Ile Asp Asp Thr
    290                 295                 300

Pro Lys Glu Gln Met Arg Lys Glu Arg Met Asp Gly Ile Glu Ser Arg
305                 310                 315                 320

Cys Arg Asn Asn Thr Val Glu Glu Asn Leu Ser Leu Trp Lys Glu Met
            325                 330                 335

Val Asn Gly Thr Glu Arg Gly Met Gln Cys Val Arg Gly Lys Leu
            340                 345                 350

Asp Met Gln Asp Pro Asn Lys Ser Leu Arg Asp Pro Val Tyr Tyr Arg
    355                 360                 365

Cys Asn Thr Asp Pro His His Arg Val Gly Ser Lys Tyr Lys Val Tyr
    370                 375                 380

Pro Thr Tyr Asp Phe Ala Cys Pro Phe Val Asp Ala Leu Glu Gly Val
385                 390                 395                 400

Thr His Ala Leu Arg Ser Ser Glu Tyr His Asp Arg Asn Ala Gln Tyr
            405                 410                 415

Tyr Arg Ile Leu Gln Asp Met Gly Leu Arg Arg Val Glu Ile Tyr Glu
            420                 425                 430

Phe Ser Arg Leu Asn Met Val Tyr Thr Leu Leu Ser Lys Arg Lys Leu
        435                 440                 445

Leu Trp Phe Val Gln Asn Lys Lys Val Glu Asp Trp Thr Asp Pro Arg
    450                 455                 460
```

-continued

```
Phe Pro Thr Val Gln Gly Ile Val Arg Arg Gly Leu Lys Val Glu Ala
465                 470                 475                 480
Leu Ile Gln Phe Ile Leu Gln Gln Gly Ala Ser Lys Asn Leu Asn Leu
            485                 490                 495
Met Glu Trp Asp Lys Leu Trp Thr Ile Asn Lys Lys Ile Ile Asp Pro
        500                 505                 510
Val Cys Ala Arg His Thr Ala Val Leu Lys Asp Gln Arg Val Ile Phe
    515                 520                 525
Thr Leu Thr Asn Gly Pro Glu Glu Pro Phe Val Arg Ile Leu Pro Arg
    530                 535                 540
His Lys Lys Phe Glu Gly Ala Gly Lys Lys Ala Thr Thr Phe Ala Asn
545                 550                 555                 560
Arg Ile Trp Leu Asp Tyr Ala Asp Ala Ala Ile Asn Lys Gly Glu
            565                 570                 575
Glu Val Thr Leu Met Asp Trp Gly Asn Ala Ile Val Lys Glu Ile Lys
        580                 585                 590
Val Glu Ser Gly Val Ile Thr Glu Leu Val Gly Glu Leu His Leu Glu
    595                 600                 605
Gly Ser Val Lys Thr Thr Lys Leu Lys Ile Thr Trp Leu Ala Asp Ile
    610                 615                 620
Glu Glu Leu Val Pro Leu Ser Leu Val Glu Phe Asp Tyr Leu Ile Ser
625                 630                 635                 640
Lys Lys Lys Leu Glu Glu Asp Glu Asp Phe Leu Asp Asn Leu Asn Pro
            645                 650                 655
Cys Thr Arg Arg Glu Ile Pro Ala Leu Gly Asp Ala Asn Met Arg Asn
        660                 665                 670
Ile Lys Arg Gly Glu Ile Gln Leu Glu Arg Lys Gly Tyr Tyr Arg
    675                 680                 685
Cys Asp Ala Pro Phe Ile Arg Ser Ser Lys Pro Val Val Leu Phe Ala
    690                 695                 700
Ile Pro Asp Gly Arg Gln Gln Ala Ser Leu Ser
705                 710                 715

<210> SEQ ID NO 11
<211> LENGTH: 1920
<212> TYPE: DNA
<213> ORGANISM: Oryza sativa
<220> FEATURE:
<221> NAME/KEY: unsure
<222> LOCATION: (139)
<223> OTHER INFORMATION: n = A, C, G or T
<220> FEATURE:
<221> NAME/KEY: unsure
<222> LOCATION: (238)
<223> OTHER INFORMATION: n = A, C, G or T
<220> FEATURE:
<221> NAME/KEY: unsure
<222> LOCATION: (431)
<223> OTHER INFORMATION: n = A, C, G or T

<400> SEQUENCE: 11
ccaatctccg gagatgatgg cggcggcaat ggggtcgcca tggctgcgca tcaggctgct        60
cccggaggtg ccgccgcgcc tcctgcggcc ccacctccgc cggccctctc cgtccgcgcc       120
tccgcctccg cctcggcgnc accggacggc gccggcggcc cggtgcgggc cgttcgcgc        180 cgtcgccgac ggcaacctcc acgtcggcgg cgcccgcacc gcgcacttca actacctntt       240
cgcgcggtcc aagggggca agttcgtgct ccgcatcgag acaccgact tcgagaggtc         300 caccaagaag tccgaggagg ccgtgctcag tgacctcgcc tggctcggcc ttgactggga       360
```

-continued

```
cgaaggcccg gatgtcggtg gggaatatgg gcccgatcgc cagtccgagc gcaattcgat    420
gtacaaacag natgccgaga agctgatgga gtctggggca gtctatcagt gcttttactc    480
cagtgaggga cttgaacaga tgaaggaaac tgcaagcaga tgcaaccttc cacctgtata    540
cattggcaag tgggggactg cttcagatgc agaaatacaa caggagttag agaaggggac    600
accttacact taccgtttcc gtgtaccgaa ggaagggtcg ttgaaaatta atgaccttat    660
tcgtggtgag gtcagttgga acttagacac gcttggtgat tcgtgatta tgagaagcaa    720 tggccagcca gtgtataact tctgtgtcac agttgatgat gctaccatgc gcatctctca    780
tgttatcaga gctgaagaac atctgccaaa cacattacgg caggctctta tttataaagc    840
acttggattt ccaatgcctt cgtttgctca tgtatcactt attctagctc ctgatagaag    900
taaactgtct aaacgtcatg ggctacttc tgtgggacag tacaaagaga tgggctattt    960
gcctcaggca atggtaaatt atttggcact tcttggttgg ggtgatggta ctgaaaatga    1020
gttcttcacc attgatgacc tagtggaaaa attcactata aatcgtgtca acaaaagtgg    1080
agcagtcttt gatgctgtaa aattaaaatg gatgaatgga caacatctaa gatcatttcc    1140
ccctgatgta ctcatcaaga gttttgagga tagatggaag gacacaggca ttctccagga    1200
gtctgaaagt ggttttgcta agaagcggc tgagcttttg aaggatggca tcgatttgat    1260
cactgatgct gacgcagccc tttcaaacct gttgtcgtat cccctccatg ctacattaag    1320
cagtgatgaa gctaaatctg tggtgcaaga caagctttct gaggttgcat caggactcat    1380
ttctgcttat gatagcggtg aactttgtca agcactagct gagggccgtg atggttggca    1440
gaagtgggtg aaaatttttg gcaaatcact taaagaaag ggaaagtcac tctttatgcc    1500
gctccgtgta ctgctgactg gcaagcttca tgggcctgac atgggcggca ccgtagtcct    1560
catacacaaa gccggcacct gtggagcggt cactcagcaa tccggtttcg taaatctcga    1620
cgagaggttc agaatcctga aggaggtgga gtgggagtca ctggtacagg agcaagagtc    1680
cccagctgaa actgccgttc ctgcttctcg ataggctgca agattcagat caatcaggga    1740 gagttttttgt tttctgtaat actccactat aaagcatagg atatgttcca ttttactacc    1800
catttctaca gttgtgagga aactatagtt tcggttttct gtagttaata aagcggaatt    1860
ttgcttagct gttctgtaat tgtcgatttg aattggattg gatggcaaag gttacgaggt    1920
```

<210> SEQ ID NO 12
<211> LENGTH: 555
<212> TYPE: PRT
<213> ORGANISM: Oryza sativa
<220> FEATURE:
<221> NAME/KEY: UNSURE
<222> LOCATION: (130)
<223> OTHER INFORMATION: Xaa = ANY AMINO ACID

<400> SEQUENCE: 12

```
Leu Arg Ile Arg Leu Leu Pro Glu Val Pro Arg Leu Leu Arg Pro
  1               5                  10                  15

His Leu Arg Arg Pro Ser Pro Ser Ala Pro Pro Pro Pro Arg Arg
             20                  25                  30

His Arg Thr Ala Pro Ala Ala Arg Cys Gly Pro Val Arg Ala Val
         35                  40                  45

Asp Gly Asn Leu His Val Gly Gly Ala Arg Thr Ala His Phe Asn Tyr
     50                  55                  60

Leu Phe Ala Arg Ser Lys Gly Gly Lys Phe Val Leu Arg Ile Glu Asp
 65                  70                  75                  80
```

```
Thr Asp Phe Glu Arg Ser Thr Lys Lys Ser Glu Glu Ala Val Leu Ser
                85                  90                  95

Asp Leu Ala Trp Leu Gly Leu Asp Trp Asp Glu Gly Pro Asp Val Gly
            100                 105                 110

Gly Glu Tyr Gly Pro Asp Arg Gln Ser Glu Arg Asn Ser Met Tyr Lys
            115                 120                 125

Gln Xaa Ala Glu Lys Leu Met Glu Ser Gly Ala Val Tyr Gln Cys Phe
        130                 135                 140

Tyr Ser Ser Glu Gly Leu Glu Gln Met Lys Glu Thr Ala Ser Arg Cys
145                 150                 155                 160

Asn Leu Pro Pro Val Tyr Ile Gly Lys Trp Gly Thr Ala Ser Asp Ala
                165                 170                 175

Glu Ile Gln Gln Glu Leu Glu Lys Gly Thr Pro Tyr Thr Tyr Arg Phe
                180                 185                 190

Arg Val Pro Lys Glu Gly Ser Leu Lys Ile Asn Asp Leu Ile Arg Gly
            195                 200                 205

Glu Val Ser Trp Asn Leu Asp Thr Leu Gly Asp Phe Val Ile Met Arg
        210                 215                 220

Ser Asn Gly Gln Pro Val Tyr Asn Phe Cys Val Thr Val Asp Asp Ala
225                 230                 235                 240

Thr Met Arg Ile Ser His Val Ile Arg Ala Glu Glu His Leu Pro Asn
                245                 250                 255

Thr Leu Arg Gln Ala Leu Ile Tyr Lys Ala Leu Gly Phe Pro Met Pro
                260                 265                 270

Ser Phe Ala His Val Ser Leu Ile Leu Ala Pro Asp Arg Ser Lys Leu
            275                 280                 285

Ser Lys Arg His Gly Ala Thr Ser Val Gly Gln Tyr Lys Glu Met Gly
        290                 295                 300

Tyr Leu Pro Gln Ala Met Val Asn Tyr Leu Ala Leu Leu Gly Trp Gly
305                 310                 315                 320

Asp Gly Thr Glu Asn Glu Phe Phe Thr Ile Asp Asp Leu Val Glu Lys
                325                 330                 335

Phe Thr Ile Asn Arg Val Asn Lys Ser Gly Ala Val Phe Asp Ala Val
                340                 345                 350

Lys Leu Lys Trp Met Asn Gly Gln His Leu Arg Ser Phe Pro Pro Asp
            355                 360                 365

Val Leu Ile Lys Ser Phe Glu Asp Arg Trp Lys Asp Thr Gly Ile Leu
        370                 375                 380

Gln Glu Ser Glu Ser Gly Phe Ala Lys Glu Ala Ala Glu Leu Leu Lys
385                 390                 395                 400

Asp Gly Ile Asp Leu Ile Thr Asp Ala Asp Ala Ala Leu Ser Asn Leu
                405                 410                 415

Leu Ser Tyr Pro Leu His Ala Thr Leu Ser Ser Asp Glu Ala Lys Ser
                420                 425                 430

Val Val Gln Asp Lys Leu Ser Glu Val Ala Ser Gly Leu Ile Ser Ala
            435                 440                 445

Tyr Asp Ser Gly Glu Leu Cys Gln Ala Leu Ala Glu Gly Arg Asp Gly
        450                 455                 460

Trp Gln Lys Trp Val Lys Ile Phe Gly Lys Ser Leu Lys Arg Lys Gly
465                 470                 475                 480

Lys Ser Leu Phe Met Pro Leu Arg Val Leu Leu Thr Gly Lys Leu His
                485                 490                 495
```

```
Gly Pro Asp Met Gly Gly Thr Val Val Leu Ile His Lys Ala Gly Thr
            500                 505                 510
Cys Gly Ala Val Thr Gln Gln Ser Gly Phe Val Asn Leu Asp Glu Arg
            515                 520                 525
Phe Arg Ile Leu Lys Glu Val Glu Trp Glu Ser Leu Val Gln Glu Gln
        530                 535                 540
Glu Ser Pro Ala Glu Thr Ala Val Pro Ala Ser
545                 550                 555

<210> SEQ ID NO 13
<211> LENGTH: 731
<212> TYPE: DNA
<213> ORGANISM: Glycine max

<400> SEQUENCE: 13
gcaaaacaaa acagagaaaa tggcgctgtt gtgtggcggc atgccatggt cgaaggtgat      60
agttcctccc attttccacc actctcacac ccctcgcacc ttcttcttcc aacgacgccg     120
tttctcaagt ctctgctctc tccgaacaac caccacccgt tcgcgttcgt ttcgctcctt     180
ctcccaccgg aaacctccac gtcggcggtg cccgaacggc cctcttcaac tacttgttcg     240
caaggtccaa aggtgggaaa tttgtgctga aattgagga cactgacttg agaggtcca      300
caagggagtc tgaggaggcc atgctcaaag atctttcttg gcttggactt gattgggatg     360
aagggcctgg tgttggaggg gattatggtc cttataggca gtctgatagg aattctttat     420
acaagcaatt tgcggataac ctacaccaat ccggtcatgt ttatcgctgc ttctgttcta     480
atgaggaact agagaaaatg aaggaggatg ctaaactaaa gcaactgcct ccagtgtaca     540
caggtaaatg ggccagtgca acaaatgagg aagtagaaga agagctagca aaaggaactc     600
cttacactta ccggttccga gtccctaaag gaagtttaaa aattaatgat caaatacgag     660
gcgaagttag ttggaacttg gatacgcttg gagattttgt gataatgagg agtaatggtc     720
agcctgttta t                                                          731

<210> SEQ ID NO 14
<211> LENGTH: 404
<212> TYPE: PRT
<213> ORGANISM: Glycine max

<400> SEQUENCE: 14

Val Arg Val Arg Phe Ala Pro Ser Pro Thr Gly Asn Leu His Val Gly
  1               5                  10                  15
Gly Ala Arg Thr Ala Leu Phe Asn Tyr Leu Phe Ala Arg Ser Lys Gly
             20                  25                  30
Gly Lys Phe Val Leu Arg Ile Glu Asp Thr Asp Leu Glu Arg Ser Thr
         35                  40                  45
Arg Glu Ser Glu Glu Ala Met Leu Lys Asp Leu Ser Trp Leu Gly Leu
     50                  55                  60
Asp Trp Asp Glu Gly Pro Gly Val Gly Gly Asp Tyr Gly Pro Tyr Arg
 65                  70                  75                  80
Gln Ser Asp Arg Asn Ser Leu Tyr Lys Gln Phe Ala Asp Asn Leu His
                 85                  90                  95
Gln Ser Gly His Val Tyr Arg Cys Phe Cys Ser Asn Glu Glu Leu Glu
            100                 105                 110
Lys Met Lys Glu Asp Ala Lys Leu Lys Gln Leu Pro Pro Val Tyr Thr
        115                 120                 125
Gly Lys Trp Ala Ser Ala Thr Asn Glu Glu Val Glu Glu Glu Leu Ala
```

```
            130                 135                 140
Lys Gly Thr Pro Tyr Thr Tyr Arg Phe Arg Val Pro Lys Gly Ser Leu
145                 150                 155                 160

Lys Ile Asn Asp Gln Ile Arg Gly Glu Val Ser Trp Asn Leu Asp Thr
                165                 170                 175

Leu Gly Asp Phe Val Ile Met Arg Ser Asn Gly Gln Pro Val Tyr Asn
            180                 185                 190

Phe Cys Val Thr Val Asp Asp Ala Thr Met Ala Ile Ser His Val Ile
        195                 200                 205

Arg Ala Glu Glu His Leu Pro Asn Thr Leu Arg Gln Ala Leu Ile Tyr
210                 215                 220

Lys Ala Leu Gly Phe Pro Met Pro His Phe Ala His Val Ser Leu Ile
225                 230                 235                 240

Leu Ala Pro Asp Arg Ser Lys Leu Ser Lys Arg His Gly Ala Thr Ser
                245                 250                 255

Val Gly Gln Phe Arg Asp Met Gly Tyr Leu Pro Gln Ala Met Val Asn
            260                 265                 270

Tyr Leu Ala Leu Leu Gly Trp Gly Asp Gly Thr Glu Asn Glu Phe Phe
        275                 280                 285

Thr Leu Glu Gln Leu Val Glu Lys Phe Thr Ile Glu Arg Val Asn Lys
290                 295                 300

Ser Gly Ala Ile Phe Asp Ser Thr Lys Leu Arg Trp Met Asn Gly Gln
305                 310                 315                 320

His Leu Arg Ser Leu Pro Ser Glu Glu Leu Asn Arg Ile Ile Gly Glu
                325                 330                 335

Arg Trp Lys Asp Ala Gly Ile Ala Thr Glu Ser Gln Gly Ile Phe Ile
            340                 345                 350

Gln Asp Ala Val Leu Leu Lys Asp Gly Ile Asp Leu Ile Thr Asp
        355                 360                 365

Ser Glu Lys Ala Leu Ser Ser Leu Leu Ser Tyr Pro Leu Tyr Glu Thr
                370                 375                 380

Leu Ala Ser Ala Glu Gly Lys Pro Ile Leu Glu Asp Gly Val Ser Glu
385                 390                 395                 400

Val Ala Lys Ser

<210> SEQ ID NO 15
<211> LENGTH: 407
<212> TYPE: DNA
<213> ORGANISM: Triticum aestivum
<220> FEATURE:
<221> NAME/KEY: unsure
<222> LOCATION: (14)
<223> OTHER INFORMATION: n = A, C, G or T
<220> FEATURE:
<221> NAME/KEY: unsure
<222> LOCATION: (250)
<223> OTHER INFORMATION: n = A, C, G or T
<220> FEATURE:
<221> NAME/KEY: unsure
<222> LOCATION: (293)
<223> OTHER INFORMATION: n = A, C, G or T
<220> FEATURE:
<221> NAME/KEY: unsure
<222> LOCATION: (341)
<223> OTHER INFORMATION: n = A, C, G or T
<220> FEATURE:
<221> NAME/KEY: unsure
<222> LOCATION: (350)..(351)
<223> OTHER INFORMATION: n = A, C, G or T
<220> FEATURE:
<221> NAME/KEY: unsure
```

```
<222> LOCATION: (383)
<223> OTHER INFORMATION: n = A, C, G or T
<220> FEATURE:
<221> NAME/KEY: unsure
<222> LOCATION: (399)
<223> OTHER INFORMATION: n = A, C, G or T
<220> FEATURE:
<221> NAME/KEY: unsure
<222> LOCATION: (401)
<223> OTHER INFORMATION: n = A, C, G or T

<400> SEQUENCE: 15
tcaataacac tcantggaaa agacaaatt cttccgctac gcacaagcta catcgctact      60
ttcagcactc tttgttcccg tcgtacaaaa tttcaaaatt ctctcagtga gcgattgcct    120
gcaaggacgc gattcgcgcc gtcaccaaca gggaatcttc atcttggttc cctacgtacg    180
gccctcttca attacctgat tgcaaaagct acacgcggta aattcatcct acgcatagag    240
gacacagatn agtcaaggac tgttcctggt gcgattgaaa aactctgcgc tgntttgaga    300
tgggggggtt taaaaaggga taaaagggct ggtccccaat ngaccgcaan ngggccttc    360 aaaaatctca aaagactttt aangttataa aaaaaaacnc nccataa                  407

<210> SEQ ID NO 16
<211> LENGTH: 79
<212> TYPE: PRT
<213> ORGANISM: Triticum aestivum
<220> FEATURE:
<221> NAME/KEY: UNSURE
<222> LOCATION: (55)
<223> OTHER INFORMATION: Xaa = ANY AMINO ACID
<220> FEATURE:
<221> NAME/KEY: UNSURE
<222> LOCATION: (69)
<223> OTHER INFORMATION: Xaa = ANY AMINO ACID

<400> SEQUENCE: 16

Lys Phe Gln Asn Ser Leu Ser Glu Arg Leu Pro Ala Arg Thr Arg Phe
 1               5                  10                  15

Ala Pro Ser Pro Thr Gly Asn Leu His Leu Gly Ser Leu Arg Thr Ala
                20                  25                  30

Leu Phe Asn Tyr Leu Ile Ala Lys Ala Thr Arg Gly Lys Phe Ile Leu
            35                  40                  45

Arg Ile Glu Asp Thr Asp Xaa Ser Arg Thr Val Pro Gly Ala Ile Glu
        50                  55                  60

Lys Leu Cys Ala Xaa Leu Arg Trp Gly Gly Leu Lys Arg Asp Lys
 65                  70                  75

<210> SEQ ID NO 17
<211> LENGTH: 2387
<212> TYPE: DNA
<213> ORGANISM: Zea mays

<400> SEQUENCE: 17
cgccgccgac atcaaggtgc tcgtcttcgg ctccaagctt gtcggcgctg ctggggcgt     60 ccccgccgcc gccacgttcg ccaaggtgcc cgcgctgaac gggatcttcc gccaggcggt    120
gcgggcgctg catgtcttaa tgcgcatcga gctcaacgca cccgtcaaat tggggaagag    180
ggatgctggt gaaaccggtg aggggaagga ggagcactg tggtgctgg ccacacagct    240 cgctagagca gtgcaggcac tcagcaagct gagcattgcc cgggcacggc tctgtgcgga    300
gagtattgct gatgctgagc ttcgggagaa gcttactggt ggcgttagcg ttgatgattt    360
gaaggggatg cttgacaatg ttttgattga ttcagatgcc gtatcagtct tgaaggggt    420
```

-continued

```
gtacaaccac ttgctcaagt tcagggactt tcttgcctgg aagcagctg tggccatggc      480 agtaattgaa gcagacagtt caattgagaa gccacaagct gctgttgaga atgaagcagc      540
cagtgtaact gagaagccac tggctggtgg ggacaaagca aagggtgaca agaagagcaa      600
gaagaagaaa actttgggta agggtacttc tgctgtgctc atgctgctta gggaccatgt      660
gacaaatgga agtactgttg ctgccatgaa ttctgcgtcg gttgcagagt gggcaacctc      720
tctgtcattg ctatttgatc ccaaatgtcc aggattggag tcacttgtgg agaaggtgaa      780
ggagattgtt gagagcaatg aagtgaggag attgcctaaa attccaaagg gtacacgcga      840
ctttggtaaa gagcaaatgg cgataaggga gcgagcattt tcaattataa ctagtgtatt      900
caagatgcat ggtgctactg cgcttgatac acccgtattt gagctgagag aaacccttat      960
gggaaaatat ggtgaagact caaagttgat atatgactta gctgatcagg gtggtgagct     1020
ttgctctttg cggtatgatc tgactgttcc atttgcccgt tatgttgcca tgaatagcat     1080
tagtgcatta aagagatacc aaatagcgaa agtatatagg agagataatc catctaaggg     1140
aagataccga gaattctacc aatgtgactt tgacattgct ggtgtatatg aacctatgga     1200
accggatttt gaggtcataa agttctgac tgaattgctg aatcagctgg atataggcac     1260
atatgagata aaattaaatc acagaaagtt gcttgatggt atgttggaga tttgtggtgt     1320 gcccctcaa agttcagaa cagtttgctc gagtattgac aaactggaca agcaaacatt     1380
cgaacaggtg aagaaggaac tggttgatga gaaaggtata tcaaatgaaa ctgcggatga     1440
aattggcaat ttagtgaaga ctaggggccc cccgttggaa gttttgatgg agttgagaaa     1500
ggagggcagc aagtttatga ataatgtagg gtctgttgct gcactgaatg agctggagat     1560
attattcaaa gctctggata aagcaaatgc aataagcaag ataactttg atttaagttt     1620 ggccaggggc cttgattact acactggtgt catatatgaa gccgttttca agggtgcagc     1680
tcaggttggc tccatagcgg ctggtggtcg gtacgacaac cttgtgggta tgtttagtgg     1740
gaagcaaatc cctgctgttg gtgtgagcct tggaattgag agagtctttg caatcatgga     1800
gcagcaggag aaagaaagaa atgagaagat ccggcctaca gagacagagg tgctggtgtc     1860
aattctggga aaggacctta ccctagctgc cgagctcgtg agcgagctgt ggaatgctgg     1920
gataaaggca gagttcaagc tcactaccag ggtggcgaac cacatcaagt atgccttgca     1980
atcaagcatt ccgtggatgg tgctagtcgg cgagtctgag ctgcagaaag gaactgtaaa     2040
gttgaaggac gttgaagcca accaggaaga agaggttgat aggaaggatt tgttcgaga      2100 gttgaagaag agattgagta aatcctaaga ggaaaatttt aggcgttgat atcatctttt     2160
gacacccatt tgacgcaaac tcaattaggg ggagaatgac attacatcat tataatttaa     2220
actgacgtga atgtttcagt ccggttggca tagggccact tgttatgttc ataaggtcat     2280
tcgaatcccc tgagtcccaa tgcattatgc tgatgaatca ggctgcagac atattgtgaa     2340
ttatattctt tttgtactac cttgaggaat gaaaagtttt tgtcctc                   2387
```

<210> SEQ ID NO 18
<211> LENGTH: 495
<212> TYPE: PRT
<213> ORGANISM: Zea mays

<400> SEQUENCE: 18

```
Met Leu Leu Arg Asp His Val Thr Asn Gly Ser Thr Val Ala Ala Met
  1               5                  10                  15

Asn Ser Ala Ser Val Ala Glu Trp Ala Thr Ser Leu Ser Leu Leu Phe
```

-continued

```
                    20                  25                  30
Asp Pro Lys Cys Pro Gly Leu Glu Ser Leu Val Glu Lys Val Lys Glu
         35                  40                  45

Ile Val Glu Ser Asn Glu Val Arg Arg Leu Pro Lys Ile Pro Lys Gly
 50                  55                  60

Thr Arg Asp Phe Gly Lys Glu Gln Met Ala Ile Arg Glu Arg Ala Phe
 65                  70                  75                  80

Ser Ile Ile Thr Ser Val Phe Lys Met His Gly Ala Thr Ala Leu Asp
                 85                  90                  95

Thr Pro Val Phe Glu Leu Arg Glu Thr Leu Met Gly Lys Tyr Gly Glu
             100                 105                 110

Asp Ser Lys Leu Ile Tyr Asp Leu Ala Asp Gln Gly Gly Glu Leu Cys
         115                 120                 125

Ser Leu Arg Tyr Asp Leu Thr Val Pro Phe Ala Arg Tyr Val Ala Met
 130                 135                 140

Asn Ser Ile Ser Ala Leu Lys Arg Tyr Gln Ile Ala Lys Val Tyr Arg
145                 150                 155                 160

Arg Asp Asn Pro Ser Lys Gly Arg Tyr Arg Glu Phe Tyr Gln Cys Asp
                 165                 170                 175

Phe Asp Ile Ala Gly Val Tyr Glu Pro Met Glu Pro Asp Phe Glu Val
             180                 185                 190

Ile Lys Val Leu Thr Glu Leu Leu Asn Gln Leu Asp Ile Gly Thr Tyr
         195                 200                 205

Glu Ile Lys Leu Asn His Arg Lys Leu Leu Asp Gly Met Leu Glu Ile
 210                 215                 220

Cys Gly Val Pro Pro Gln Lys Phe Arg Thr Val Cys Ser Ser Ile Asp
225                 230                 235                 240

Lys Leu Asp Lys Gln Thr Phe Glu Gln Val Lys Lys Glu Leu Val Asp
                 245                 250                 255

Glu Lys Gly Ile Ser Asn Glu Thr Ala Asp Glu Ile Gly Asn Leu Val
             260                 265                 270

Lys Thr Arg Gly Pro Pro Leu Glu Val Leu Met Glu Leu Arg Lys Glu
         275                 280                 285

Gly Ser Lys Phe Met Asn Asn Val Gly Ser Val Ala Ala Leu Asn Glu
 290                 295                 300

Leu Glu Ile Leu Phe Lys Ala Leu Asp Lys Ala Asn Ala Ile Ser Lys
305                 310                 315                 320

Ile Thr Phe Asp Leu Ser Leu Ala Arg Gly Leu Asp Tyr Tyr Thr Gly
                 325                 330                 335

Val Ile Tyr Glu Ala Val Phe Lys Gly Ala Ala Gln Val Gly Ser Ile
             340                 345                 350

Ala Ala Gly Gly Arg Tyr Asp Asn Leu Val Gly Met Phe Ser Gly Lys
         355                 360                 365

Gln Ile Pro Ala Val Gly Val Ser Leu Gly Ile Glu Arg Val Phe Ala
 370                 375                 380

Ile Met Glu Gln Gln Glu Lys Glu Arg Asn Glu Lys Ile Arg Pro Thr
385                 390                 395                 400

Glu Thr Glu Val Leu Val Ser Ile Leu Gly Lys Asp Leu Thr Leu Ala
                 405                 410                 415

Ala Glu Leu Val Ser Glu Leu Trp Asn Ala Gly Ile Lys Ala Glu Phe
             420                 425                 430

Lys Leu Thr Thr Arg Val Ala Asn His Ile Lys Tyr Ala Leu Gln Ser
         435                 440                 445
```

```
Ser Ile Pro Trp Met Val Leu Val Gly Glu Ser Glu Leu Gln Lys Gly
    450                 455                 460

Thr Val Lys Leu Lys Asp Val Glu Ala Asn Gln Glu Glu Val Asp
465                 470                 475                 480

Arg Lys Asp Phe Val Arg Glu Leu Lys Lys Arg Leu Ser Lys Ser
                485                 490                 495
```

<210> SEQ ID NO 19
<211> LENGTH: 754
<212> TYPE: DNA
<213> ORGANISM: Glycine max
<220> FEATURE:
<221> NAME/KEY: unsure
<222> LOCATION: (18)
<223> OTHER INFORMATION: n = A, C, G or T
<220> FEATURE:
<221> NAME/KEY: unsure
<222> LOCATION: (610)
<223> OTHER INFORMATION: n = A, C, G or T
<220> FEATURE:
<221> NAME/KEY: unsure
<222> LOCATION: (713)
<223> OTHER INFORMATION: n = A, C, G or T
<220> FEATURE:
<221> NAME/KEY: unsure
<222> LOCATION: (720)
<223> OTHER INFORMATION: n = A, C, G or T
<220> FEATURE:
<221> NAME/KEY: unsure
<222> LOCATION: (740)
<223> OTHER INFORMATION: n = A, C, G or T

<400> SEQUENCE: 19

```
ggaacatgga tattattngt gttcccgggg ttatggctga agcagagctt atagcttcta    60
tcgtcacttt gtttaagcga ataggaatta cagaatcaga tgtcggattt aaggtttcca   120
gtcgaaaggt tctgcaagaa gtattaaatt gttattcagt accagaaaat ttatttggca   180
aggtctgcgt cattattgat aaaattgaga aaattccagc tgacgagata agaaagagt    240
tgaaagctgt tggtctatct caagaggctg tccaggagct attgcaagtc ctttctgtga   300
agtcattgac cgagttagaa gagagacttg ggagcagtgg ggaagcagtt gctgatctga   360
aacagctatt ctcccttgct gaaaaaattg gttactctaa atggcttcaa tttgatgcat   420
cagttgttcg aggtcttgct tactacactg gcattgtatt tgagggtttt gaccgagaag   480
gaaagctgcg agctatctgt ggtggtggtc gatatgatca tttgttctca acttttggtg   540
ctgatgacat tgctgcatgt ggttttggat ttggtgatgc aagtcatagt ggaattgctc   600
aaaagagaan ggtctgttac cgggaagctt aacttgcaaa tagatgacat tgtgtgtgcc   660
ttggaccaaa gatcttcaag ggatgtgctg ctatgggccc caacaatctc agngaaaaan   720
ggcaaattgt tgaagttggn tttgggaaaa caaa                                754
```

<210> SEQ ID NO 20
<211> LENGTH: 243
<212> TYPE: PRT
<213> ORGANISM: Glycine max
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (203)
<223> OTHER INFORMATION: Xaa = ANY AMINO ACID
<220> FEATURE:
<221> NAME/KEY: UNSURE

```
<222> LOCATION: (235)
<223> OTHER INFORMATION: Xaa = ANY AMINO ACID
<220> FEATURE:
<221> NAME/KEY: UNSURE
<222> LOCATION: (238)
<223> OTHER INFORMATION: Xaa = ANY AMINO ACID

<400> SEQUENCE: 20
```

| | | | | | | | | | | | | | | |
|---|---|---|---|---|---|---|---|---|---|---|---|---|---|---|
|Asn|Met|Asp|Ile|Ile|Xaa|Val|Pro|Gly|Val|Met|Ala|Glu|Ala|Glu|Leu|
|1| | | |5| | | | |10| | | | |15|
|Ile|Ala|Ser|Ile|Val|Thr|Leu|Phe|Lys|Arg|Ile|Gly|Ile|Thr|Glu|Ser|
| | | |20| | | | |25| | | | |30| | |
|Asp|Val|Gly|Phe|Lys|Val|Ser|Ser|Arg|Lys|Val|Leu|Gln|Glu|Val|Leu|
| | |35| | | | |40| | | | |45| | | |
|Asn|Cys|Tyr|Ser|Val|Pro|Glu|Asn|Leu|Phe|Gly|Lys|Val|Cys|Val|Ile|
| |50| | | | |55| | | | |60| | | | |
|Ile|Asp|Lys|Ile|Glu|Lys|Ile|Pro|Ala|Asp|Glu|Ile|Lys|Lys|Glu|Leu|
|65| | | | |70| | | | |75| | | | |80|
|Lys|Ala|Val|Gly|Leu|Ser|Gln|Glu|Ala|Val|Gln|Glu|Leu|Leu|Gln|Val|
| | | | |85| | | | |90| | | | |95| |
|Leu|Ser|Val|Lys|Ser|Leu|Thr|Glu|Leu|Glu|Arg|Leu|Gly|Ser|Ser|
| | | |100| | | | |105| | | | |110| | |
|Gly|Glu|Ala|Val|Ala|Asp|Leu|Lys|Gln|Leu|Phe|Ser|Leu|Ala|Glu|Lys|
| | |115| | | | |120| | | | |125| | | |
|Ile|Gly|Tyr|Ser|Lys|Trp|Leu|Gln|Phe|Asp|Ala|Ser|Val|Val|Arg|Gly|
| |130| | | | |135| | | | |140| | | | |
|Leu|Ala|Tyr|Tyr|Thr|Gly|Ile|Val|Phe|Glu|Gly|Phe|Asp|Arg|Glu|Gly|
|145| | | | |150| | | | |155| | | | |160|
|Lys|Leu|Arg|Ala|Ile|Cys|Gly|Gly|Arg|Tyr|Asp|His|Leu|Phe|Ser|
| | | | |165| | | | |170| | | | |175| |
|Thr|Phe|Gly|Ala|Asp|Asp|Ile|Ala|Ala|Cys|Gly|Phe|Gly|Phe|Gly|Asp|
| | | |180| | | | |185| | | | |190| | | |
|Ala|Ser|His|Ser|Gly|Ile|Ala|Gln|Lys|Arg|Xaa|Val|Cys|Tyr|Arg|Glu|
| | |195| | | | |200| | | | |205| | | | |
|Ala|Leu|Ala|Asn|Arg|His|Cys|Val|Cys|Leu|Gly|Pro|Lys|Ile|Phe|Lys|
| |210| | | | |215| | | | |220| | | | |
|Gly|Cys|Ala|Ala|Met|Gly|Pro|Asn|Asn|Leu|Xaa|Glu|Lys|Xaa|Gln|Ile|
|225| | | | |230| | | | |235| | | | |240|
|Val|Glu|Val| | | | | | | | | | | | | |

```
<210> SEQ ID NO 21
<211> LENGTH: 1164
<212> TYPE: DNA
<213> ORGANISM: Triticum aestivum

<400> SEQUENCE: 21
gaagcttggg attacatctt ctgatgtggg gatcagactg tccagccgaa aggttctaca      60
ggccgtgttg gatatgtact ccgtaccaca acacttgttt actcaagttt gtgttattgt     120
tgacaagctg gggaaactga gtagggaaga aattgagaag gaattgattt caactggcct     180
gtcatctgaa gcagtacagg gcatcattga agtgctctct ctcaagtcac tgtccaaact     240
tgaagaggtg ctaggctcag gtgttgaagc cgttgctgac ttgaagaagc tcttctcgct     300
tgctgagcaa tatggttatt ctgattggat ctgtttcgat gcatctgttg ttcgtggcct     360
tgcatactac acaggattg ttttgaggc ttttgatagg aaggggaac tgagagcgat      420 ttgtggtggg gggaggtatg acaggctact gtcaacattt ggaactgaag atgtaccagc     480
```

-continued

```
ctgtggcttt ggatttggag atgctgtcat agtggagctg ctgaaagaaa agggtctttt      540
gcctgacctg ccacgtcaaa tagatgacat tgtgttccca ttggacgagg agcttgaggg      600
gccagcatct agtgttgcat cctgtctgcg gaagaagggc agatctgtag accttgtaga      660
agacaagcgt ctgaaatggg tgttcaaaca tgctgagagg ataaacgcta gcaggctgat      720
cttggttggg aaatccgagt gggagcgagg catggtccgt gtgaagatac tatcaaccag      780
agaagagttc gaggtcaagg cgggcgaatt gcagtagctg ttagctgatc tggtcgattt      840
gaaggtttga cttgtcccct tcttctttc tgatcatctt caacactgta agttttgcaa       900
ttcacgtcgt gtatacaaac aattaggtgg ctttgaatgc tattgccatc ttctttcgga      960
tcattcacct tgcaacaaac aaagaaattg taggttttgc cattcaccaa catgtattga     1020
gaatgccttt gctgcctgag aaaaaaaaaa aaaaaaaaaa aaaaaaaaaa aaaaaaaaaa     1080
aaaaaaaaaa aaaaaaaaaa aaaaaaaaaa aaaaaaaaaa aaaaaaaaaa aaaaaaaaaa     1140
aaaaaaaaaa aaaaaaaaaa aaaa                                            1164
```

<210> SEQ ID NO 22
<211> LENGTH: 271
<212> TYPE: PRT
<213> ORGANISM: Triticum aestivum

<400> SEQUENCE: 22

```
Lys Leu Gly Ile Thr Ser Ser Asp Val Gly Ile Arg Leu Ser Ser Arg
  1               5                  10                  15

Lys Val Leu Gln Ala Val Leu Asp Met Tyr Ser Val Pro Gln His Leu
             20                  25                  30

Phe Thr Gln Val Cys Val Ile Val Asp Lys Leu Gly Lys Leu Ser Arg
         35                  40                  45

Glu Glu Ile Glu Lys Glu Leu Ile Ser Thr Gly Leu Ser Ser Glu Ala
     50                  55                  60

Val Gln Gly Ile Ile Glu Val Leu Ser Leu Lys Ser Leu Ser Lys Leu
 65                  70                  75                  80

Glu Glu Val Leu Gly Ser Gly Val Glu Ala Val Ala Asp Leu Lys Lys
                 85                  90                  95

Leu Phe Ser Leu Ala Glu Gln Tyr Gly Tyr Ser Asp Trp Ile Cys Phe
            100                 105                 110

Asp Ala Ser Val Val Arg Gly Leu Ala Tyr Tyr Thr Gly Ile Val Phe
        115                 120                 125

Glu Ala Phe Asp Arg Glu Gly Glu Leu Arg Ala Ile Cys Gly Gly Gly
    130                 135                 140

Arg Tyr Asp Arg Leu Leu Ser Thr Phe Gly Thr Glu Asp Val Pro Ala
145                 150                 155                 160

Cys Gly Phe Gly Phe Gly Asp Ala Val Ile Val Glu Leu Leu Lys Glu
                165                 170                 175

Lys Gly Leu Leu Pro Asp Leu Pro Arg Gln Ile Asp Ile Val Phe
            180                 185                 190

Pro Leu Asp Glu Glu Leu Glu Gly Pro Ala Ser Ser Val Ala Ser Cys
        195                 200                 205

Leu Arg Lys Lys Gly Arg Ser Val Asp Leu Val Glu Asp Lys Arg Leu
    210                 215                 220

Lys Trp Val Phe Lys His Ala Glu Arg Ile Asn Ala Ser Arg Leu Ile
225                 230                 235                 240

Leu Val Gly Lys Ser Glu Trp Glu Arg Gly Met Val Arg Val Lys Ile
```

245                 250                 255
Leu Ser Thr Arg Glu Glu Phe Glu Val Lys Ala Gly Glu Leu Gln
         260                 265                 270

<210> SEQ ID NO 23
<211> LENGTH: 913
<212> TYPE: DNA
<213> ORGANISM: Zea mays
<220> FEATURE:
<221> NAME/KEY: unsure
<222> LOCATION: (486)
<223> OTHER INFORMATION: n = A, C, G or T
<220> FEATURE:
<221> NAME/KEY: unsure
<222> LOCATION: (677)
<223> OTHER INFORMATION: n = A, C, G or T
<220> FEATURE:
<221> NAME/KEY: unsure
<222> LOCATION: (742)
<223> OTHER INFORMATION: n = A, C, G or T
<220> FEATURE:
<221> NAME/KEY: unsure
<222> LOCATION: (810)
<223> OTHER INFORMATION: n = A, C, G or T
<220> FEATURE:
<221> NAME/KEY: unsure
<222> LOCATION: (824)
<223> OTHER INFORMATION: n = A, C, G or T
<220> FEATURE:
<221> NAME/KEY: unsure
<222> LOCATION: (851)
<223> OTHER INFORMATION: n = A, C, G or T
<220> FEATURE:
<221> NAME/KEY: unsure
<222> LOCATION: (889)
<223> OTHER INFORMATION: n = A, C, G or T
<220> FEATURE:
<221> NAME/KEY: unsure
<222> LOCATION: (893)
<223> OTHER INFORMATION: n = A, C, G or T
<220> FEATURE:
<221> NAME/KEY: unsure
<222> LOCATION: (910)
<223> OTHER INFORMATION: n = A, C, G or T

<400> SEQUENCE: 23

```
gtttctataa tccttatatt cctcaagtgc tggaggaatt gagtaacaaa ggcttgatca      60
aggagagtga gggtgcccga gttatattta ttcaaggtca tcaaatccct ttgattgttg     120
ttaagagtga tggtggcttc aactatgcct caacagactt aactgctctt tggtatcggc     180
tcaatgttga gcaggcagag tgatcatat atgttacaga tgttggtcag cagcagcact     240
ttgacatggt tttcagtgct gcaaagatgg ccggttggct cccagatcca agtgaaaaga     300
agtttccgaa acaagccat gttggatttg gtcttgttct tggttcaaga tggcaagcgg     360
ttccgaaccc gcagtactga ggttgttcga ttggtagagc tacttgatga ggctaaatct     420
cggagcaaat cagaactact acaacggctc actgaaaatg gcaaaattgt tgactggacg     480
gatgangaat tagagcaaac ttcagaggct gttggatatg gtgctgtgaa gtacgctgat     540
ctaaaaaata acaggctcac taattacaca tttagttttg aacaaatgct gagcgataag     600
ggaaatactg ctgtgtacct tcagtatgca catgctcgta tttgttccat tattcggaaa     660
tccaacaaga acgtggnaga ctgaagagat ggagccattt ctctcgacca tccggattag     720
cgctgttggg gctgtatctt anccgatttg cagagttgtt gaagaggatc acgaactact     780
ccaaatttgt gtgtgaatac tgtcaatcan ctgaaagtca caanatcata caactgcaag     840
tggtgggtcc ngaggaacac cggtgtgctt gcaacgacgc gtttcatcna agnctcaccg     900
```
ctcggatacn cat                                                                 913

<210> SEQ ID NO 24
<211> LENGTH: 221
<212> TYPE: PRT
<213> ORGANISM: Zea mays
<220> FEATURE:
<221> NAME/KEY: UNSURE
<222> LOCATION: (96)
<223> OTHER INFORMATION: Xaa = ANY AMINO ACID
<220> FEATURE:
<221> NAME/KEY: UNSURE
<222> LOCATION: (156)
<223> OTHER INFORMATION: Xaa = ANY AMINO ACID
<220> FEATURE:
<221> NAME/KEY: UNSURE
<222> LOCATION: (220)
<223> OTHER INFORMATION: Xaa = ANY AMINO ACID

<400> SEQUENCE: 24

Phe Tyr Asn Pro Tyr Ile Pro Gln Val Leu Glu Glu Leu Ser Asn Lys
 1               5                  10                  15

Gly Leu Ile Lys Glu Ser Glu Gly Ala Arg Val Ile Phe Ile Gln Gly
             20                  25                  30

His Gln Ile Pro Leu Ile Val Val Lys Ser Asp Gly Gly Phe Asn Tyr
         35                  40                  45

Ala Ser Thr Asp Leu Thr Ala Leu Trp Tyr Arg Leu Asn Val Glu Gln
     50                  55                  60

Ala Glu Trp Ile Ile Tyr Val Thr Asp Val Gly Gln Gln Gln His Phe
 65                  70                  75                  80

Asp Met Val Phe Ser Ala Ala Lys Met Ala Gly Trp Leu Pro Asp Xaa
                 85                  90                  95

Glu Lys Lys Phe Pro Lys Thr Ser His Val Gly Phe Gly Leu Phe Leu
            100                 105                 110

Val Gln Asp Gly Lys Arg Phe Arg Thr Arg Ser Thr Glu Val Val Arg
        115                 120                 125

Leu Val Glu Leu Leu Asp Glu Ala Lys Ser Arg Ser Lys Ser Glu Leu
    130                 135                 140

Thr Glu Asn Gly Lys Ile Val Asp Trp Thr Asp Xaa Glu Leu Glu Gln
145                 150                 155                 160

Thr Ser Glu Ala Val Gly Tyr Gly Ala Val Lys Tyr Ala Asp Leu Lys
                165                 170                 175

Asn Asn Arg Leu Thr Asn Tyr Thr Phe Ser Phe Glu Gln Met Leu Ser
            180                 185                 190

Asp Lys Gly Asn Thr Ala Val Tyr Leu Gln Tyr Ala His Ala Arg Ile
        195                 200                 205

Cys Ser Ile Ile Arg Lys Ser Asn Lys Asn Val Xaa Asp
    210                 215                 220

<210> SEQ ID NO 25
<211> LENGTH: 551
<212> TYPE: DNA
<213> ORGANISM: Oryza sp.
<220> FEATURE:
<221> NAME/KEY: unsure
<222> LOCATION: (274)
<223> OTHER INFORMATION: n = A, C, G or T
<220> FEATURE:
<221> NAME/KEY: unsure
<222> LOCATION: (391)
<223> OTHER INFORMATION: n = A, C, G or T
<220> FEATURE:
<221> NAME/KEY: unsure

```
<222> LOCATION: (398)
<223> OTHER INFORMATION: n = A, C, G or T
<220> FEATURE:
<221> NAME/KEY: unsure
<222> LOCATION: (407)
<223> OTHER INFORMATION: n = A, C, G or T
<220> FEATURE:
<221> NAME/KEY: unsure
<222> LOCATION: (429)
<223> OTHER INFORMATION: n = A, C, G or T
<220> FEATURE:
<221> NAME/KEY: unsure
<222> LOCATION: (449)
<223> OTHER INFORMATION: n = A, C, G or T
<220> FEATURE:
<221> NAME/KEY: unsure
<222> LOCATION: (454)
<223> OTHER INFORMATION: n = A, C, G or T
<220> FEATURE:
<221> NAME/KEY: unsure
<222> LOCATION: (466)
<223> OTHER INFORMATION: n = A, C, G or T
<220> FEATURE:
<221> NAME/KEY: unsure
<222> LOCATION: (471)
<223> OTHER INFORMATION: n = A, C, G or T
<220> FEATURE:
<221> NAME/KEY: unsure
<222> LOCATION: (475)
<223> OTHER INFORMATION: n = A, C, G or T
<220> FEATURE:
<221> NAME/KEY: unsure
<222> LOCATION: (488)
<223> OTHER INFORMATION: n = A, C, G or T
<220> FEATURE:
<221> NAME/KEY: unsure
<222> LOCATION: (494)
<223> OTHER INFORMATION: n = A, C, G or T
<220> FEATURE:
<221> NAME/KEY: unsure
<222> LOCATION: (497)
<223> OTHER INFORMATION: n = A, C, G or T
<220> FEATURE:
<221> NAME/KEY: unsure
<222> LOCATION: (506)
<223> OTHER INFORMATION: n = A, C, G or T
<220> FEATURE:
<221> NAME/KEY: unsure
<222> LOCATION: (513)
<223> OTHER INFORMATION: n = A, C, G or T
<220> FEATURE:
<221> NAME/KEY: unsure
<222> LOCATION: (517)
<223> OTHER INFORMATION: n = A, C, G or T
<220> FEATURE:
<221> NAME/KEY: unsure
<222> LOCATION: (520)
<223> OTHER INFORMATION: n = A, C, G or T
<220> FEATURE:
<221> NAME/KEY: unsure
<222> LOCATION: (530)
<223> OTHER INFORMATION: n = A, C, G or T
<220> FEATURE:
<221> NAME/KEY: unsure
<222> LOCATION: (541)
<223> OTHER INFORMATION: n = A, C, G or T
<220> FEATURE:
<221> NAME/KEY: unsure
<222> LOCATION: (546)
<223> OTHER INFORMATION: n = A, C, G or T

<400> SEQUENCE: 25
cttacagctg aacacagtgt acagagcgtc gagcaacaac tctgtacatt aatcacatct      60
tccctgcgtg caacagtacc tgacctggat gtggaaccga tgcttgaagt ctcaaaacca    120
ggttttgggg attaccagtg caacaatgct atgagtgtat tttcaagaat aagaggatcc    180
```

```
gcaacaaact tccgtaaccc catggcagtt gggcaggcaa ttgcaaataa cctccccag    240 tcaaatatta tcgaatccat ctctgttgcc gganctggtt acattaacat aacgttatcc    300
agcaattgga ttgcacagag gatacaaaga catgcttggt tgtgggaatc aaaacatggg    360
gaacaatcct taacctgttt aagaaggcaa ntgctggntt tttcaanccc caataattgc    420
aaaaagaana tgcaagttgg gcaataatna aggncaacaa taaatngggg natanccccaa    480 ctcaaaangg ttgnggntca caaaanggtt aanttcntcn acgtaaacan gttgggaaac    540 ngggnacac a    551
```

<210> SEQ ID NO 26
<211> LENGTH: 68
<212> TYPE: PRT
<213> ORGANISM: Oryza sp.
<220> FEATURE:
<221> NAME/KEY: UNSURE
<222> LOCATION: (51)
<223> OTHER INFORMATION: Xaa = ANY AMINO ACID

<400> SEQUENCE: 26

```
Phe Gly Asp Tyr Gln Cys Asn Asn Ala Met Ser Val Phe Ser Arg Ile
 1               5                  10                  15

Arg Gly Ser Ala Thr Asn Phe Arg Asn Pro Met Ala Val Gly Gln Ala
            20                  25                  30

Ile Ala Asn Asn Leu Pro Gln Ser Asn Ile Ile Glu Ser Ile Ser Val
        35                  40                  45

Ala Gly Xaa Gly Tyr Ile Asn Ile Thr Leu Ser Ser Asn Trp Ile Ala
    50                  55                  60

Gln Arg Ile Gln
 65
```

<210> SEQ ID NO 27
<211> LENGTH: 411
<212> TYPE: DNA
<213> ORGANISM: Glycine max
<220> FEATURE:
<221> NAME/KEY: unsure
<222> LOCATION: (18)
<223> OTHER INFORMATION: n = A, C, G or T
<220> FEATURE:
<221> NAME/KEY: unsure
<222> LOCATION: (35)
<223> OTHER INFORMATION: n = A, C, G or T
<220> FEATURE:
<221> NAME/KEY: unsure
<222> LOCATION: (51)
<223> OTHER INFORMATION: n = A, C, G or T
<220> FEATURE:
<221> NAME/KEY: unsure
<222> LOCATION: (159)
<223> OTHER INFORMATION: n = A, C, G or T
<220> FEATURE:
<221> NAME/KEY: unsure
<222> LOCATION: (165)
<223> OTHER INFORMATION: n = A, C, G or T
<220> FEATURE:
<221> NAME/KEY: unsure
<222> LOCATION: (281)
<223> OTHER INFORMATION: n = A, C, G or T
<220> FEATURE:
<221> NAME/KEY: unsure
<222> LOCATION: (286)
<223> OTHER INFORMATION: n = A, C, G or T
<220> FEATURE:
<221> NAME/KEY: unsure
<222> LOCATION: (288)
<223> OTHER INFORMATION: n = A, C, G or T
<220> FEATURE:

```
<221> NAME/KEY: unsure
<222> LOCATION: (325)
<223> OTHER INFORMATION: n = A, C, G or T
<220> FEATURE:
<221> NAME/KEY: unsure
<222> LOCATION: (342)
<223> OTHER INFORMATION: n = A, C, G or T
<220> FEATURE:
<221> NAME/KEY: unsure
<222> LOCATION: (373)
<223> OTHER INFORMATION: n = A, C, G or T

<400> SEQUENCE: 27
gttgagggtg tagacatncc acttattgct gtganaagag atggtggcta naactatttt      60
acaactgatc tagcatcact ttggtatcgt ctaaatgaag aaaaacttga atggattgta     120
tatgttacag atattgggca gcaacagcac tttgatatnc tattnaaggc ctataggcgt     180
gcaggttggt taccaaagga tgagaatgcg tatccaaaat gtactcatat aggttttggt     240
cttgttcttg gggaagatgg aaaacgattt cggactcgca ncagtnangt tgttcgatta     300
gttgattact tgatgaagct aaaangcgct gtaaaattgc cntcttgaaa cgtgatacaa     360
ctaaaggatt ggnctgaagg aggagatcga gaaaacatcc gaagcagttg g             411

<210> SEQ ID NO 28
<211> LENGTH: 115
<212> TYPE: PRT
<213> ORGANISM: Glycine max
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (12)
<223> OTHER INFORMATION: Xaa = ANY AMINO ACID
<220> FEATURE:
<221> NAME/KEY: UNSURE
<222> LOCATION: (17)
<223> OTHER INFORMATION: Xaa = ANY AMINO ACID
<220> FEATURE:
<221> NAME/KEY: UNSURE
<222> LOCATION: (53)
<223> OTHER INFORMATION: Xaa = ANY AMINO ACID
<220> FEATURE:
<221> NAME/KEY: UNSURE
<222> LOCATION: (55)
<223> OTHER INFORMATION: Xaa = ANY AMINO ACID
<220> FEATURE:
<221> NAME/KEY: UNSURE
<222> LOCATION: (94)
<223> OTHER INFORMATION: Xaa = ANY AMINO ACID
<220> FEATURE:
<221> NAME/KEY: UNSURE
<222> LOCATION: (96)
<223> OTHER INFORMATION: Xaa = ANY AMINO ACID
<220> FEATURE:
<221> NAME/KEY: UNSURE
<222> LOCATION: (109)
<223> OTHER INFORMATION: Xaa = ANY AMINO ACID

<400> SEQUENCE: 28

Val Glu Gly Val Asp Xaa Pro Leu Ile Ala Val Xaa Arg Asp Gly Gly
 1               5                  10                  15

Xaa Asn Tyr Phe Thr Thr Asp Leu Ala Ser Leu Trp Tyr Arg Leu Asn
            20                  25                  30

Glu Glu Lys Leu Glu Trp Ile Val Tyr Val Thr Asp Ile Gly Gln Gln
        35                  40                  45

Gln His Phe Asp Xaa Leu Xaa Lys Ala Tyr Arg Arg Ala Gly Trp Leu
    50                  55                  60
```

```
Pro Lys Asp Glu Asn Ala Tyr Pro Lys Cys Thr His Ile Gly Phe Gly
 65                  70                  75                  80

Leu Val Leu Gly Glu Asp Gly Lys Arg Phe Arg Thr Arg Xaa Ser Xaa
                 85                  90                  95

Val Val Arg Leu Val Asp Tyr Leu Met Lys Leu Lys Xaa Ala Val Lys
            100                 105                 110

Leu Pro Ser
        115

<210> SEQ ID NO 29
<211> LENGTH: 565
<212> TYPE: DNA
<213> ORGANISM: Triticum sp.
<220> FEATURE:
<221> NAME/KEY: unsure
<222> LOCATION: (350)
<223> OTHER INFORMATION: n = A, C, G or T
<220> FEATURE:
<221> NAME/KEY: unsure
<222> LOCATION: (378)
<223> OTHER INFORMATION: n = A, C, G or T
<220> FEATURE:
<221> NAME/KEY: unsure
<222> LOCATION: (408)
<223> OTHER INFORMATION: n = A, C, G or T
<220> FEATURE:
<221> NAME/KEY: unsure
<222> LOCATION: (414)
<223> OTHER INFORMATION: n = A, C, G or T
<220> FEATURE:
<221> NAME/KEY: unsure
<222> LOCATION: (432)
<223> OTHER INFORMATION: n = A, C, G or T
<220> FEATURE:
<221> NAME/KEY: unsure
<222> LOCATION: (433)
<223> OTHER INFORMATION: n = A, C, G or T
<220> FEATURE:
<221> NAME/KEY: unsure
<222> LOCATION: (444)
<223> OTHER INFORMATION: n = A, C, G or T
<220> FEATURE:
<221> NAME/KEY: unsure
<222> LOCATION: (452)
<223> OTHER INFORMATION: n = A, C, G or T
<220> FEATURE:
<221> NAME/KEY: unsure
<222> LOCATION: (458)
<223> OTHER INFORMATION: n = A, C, G or T
<220> FEATURE:
<221> NAME/KEY: unsure
<222> LOCATION: (466)
<223> OTHER INFORMATION: n = A, C, G or T
<220> FEATURE:
<221> NAME/KEY: unsure
<222> LOCATION: (487)
<223> OTHER INFORMATION: n = A, C, G or T
<220> FEATURE:
<221> NAME/KEY: unsure
<222> LOCATION: (494)
<223> OTHER INFORMATION: n = A, C, G or T
<220> FEATURE:
<221> NAME/KEY: unsure
<222> LOCATION: (503)
<223> OTHER INFORMATION: n = A, C, G or T
<220> FEATURE:
<221> NAME/KEY: unsure
<222> LOCATION: (523)
<223> OTHER INFORMATION: n = A, C, G or T
<220> FEATURE:
<221> NAME/KEY: unsure
<222> LOCATION: (535)
<223> OTHER INFORMATION: n = A, C, G or T
<220> FEATURE:
```

```
<221> NAME/KEY: unsure
<222> LOCATION: (539)
<223> OTHER INFORMATION: n = A, C, G or T
<220> FEATURE:
<221> NAME/KEY: unsure
<222> LOCATION: (548)
<223> OTHER INFORMATION: n = A, C, G or T
<220> FEATURE:
<221> NAME/KEY: unsure
<222> LOCATION: (555)
<223> OTHER INFORMATION: n = A, C, G or T

<400> SEQUENCE: 29
tgtttttcaa ggctgccagg atggctggtt ggcttccaga tccaaaggaa aagaagttcc      60
caaaaacgag tcatgttggg tttggccttg ttcttggagc agatggcaag cgcttccgaa     120
ctcgtagtac tgaggttgtt cggttgggaa gacctacttg atgaggctaa atctcgaagt     180
aaatcaagaa cttctccaag cgtctcactg gaaaatggta aaattgttga ctggactgat     240
gaaggaacta gagcaaact tcaaaaggca gtaagatatg cgctgtcaa agtatgcggg       300
tctgaaagaa taaccgactg actaattaca cttcaacttt gattcaagan ctaagtgaca     360
agggaaatac tgctgtcnac ttcaataagc caagcccgta cctcccanca ttcnaaaacc     420
caacatggtg tnnaaaacta aaangatggg anattccncc tgccanccaa atagctgcct     480
gggacgnact aacngtatgc aanatgttaa aaggatgaca acncttccaa tgtcngggng     540
aaactatnac taccnaagta aaagt                                          565

<210> SEQ ID NO 30
<211> LENGTH: 33
<212> TYPE: PRT
<213> ORGANISM: Triticum sp.

<400> SEQUENCE: 30

Glu Lys Lys Phe Pro Lys Thr Ser His Val Gly Phe Gly Leu Val Leu
 1               5                  10                  15
Gly Ala Asp Gly Lys Arg Phe Arg Thr Arg Ser Thr Glu Val Val Arg
                20                  25                  30
Leu

<210> SEQ ID NO 31
<211> LENGTH: 546
<212> TYPE: DNA
<213> ORGANISM: Oryza sp.
<220> FEATURE:
<221> NAME/KEY: unsure
<222> LOCATION: (448)
<223> OTHER INFORMATION: n = A, C, G or T
<220> FEATURE:
<221> NAME/KEY: unsure
<222> LOCATION: (512)
<223> OTHER INFORMATION: n = A, C, G or T

<400> SEQUENCE: 31
atcactattt cccctgatg tactcatcaa gagttttgag gatagatgga aggacacagg       60
cattctccag gagtctgaaa gtggttttgc taaagaagcg gctgagcttt tgaaggatgg     120
catcgatttg atcactgatg ctgacgcagc cctttcaaac ctgttgtcgt atcccctcca     180
tgctacatta agcagtgatg aagctaaatc tgtggtgcaa gacaagcttt ctgaggttgc     240
atcaggactc atttctgctt atgatagcgg tgaactttgt caagcactag ctgagggccg     300
tgatggttgg cagaagtggg tgaaaatttt tggcaaatca cttaaaagaa agggaaagtc     360
actctttatg ccgctccgtg tactgctgac tggcaagctt catgggcctg acatgggcgg     420
```

-continued

```
caccgtagtc ctcatacaca aagccggnac tgtggagcgg tcactcaaca atccggtttc      480
gtaaatctcg acgagaggtc agaatcctga angagtggag tggagtcact ggtacaggac      540
aagatc                                                                 546
```

<210> SEQ ID NO 32
<211> LENGTH: 147
<212> TYPE: PRT
<213> ORGANISM: Oryza sp.

<400> SEQUENCE: 32

```
Pro Pro Asp Val Leu Ile Lys Ser Phe Glu Asp Arg Trp Lys Asp Thr
 1               5                  10                  15

Gly Ile Leu Gln Glu Ser Glu Ser Gly Phe Ala Lys Glu Ala Ala Glu
                20                  25                  30

Leu Leu Lys Asp Gly Ile Asp Leu Ile Thr Asp Ala Asp Ala Ala Leu
            35                  40                  45

Ser Asn Leu Leu Ser Tyr Pro Leu His Ala Thr Leu Ser Ser Asp Glu
        50                  55                  60

Ala Lys Ser Val Val Gln Asp Lys Leu Ser Glu Val Ala Ser Gly Leu
    65                  70                  75                  80

Ile Ser Ala Tyr Asp Ser Gly Glu Leu Cys Gln Ala Leu Ala Glu Gly
                85                  90                  95

Arg Asp Gly Trp Gln Lys Trp Val Lys Ile Phe Gly Lys Ser Leu Lys
               100                 105                 110

Arg Lys Gly Lys Ser Leu Phe Met Pro Leu Arg Val Leu Leu Thr Gly
           115                 120                 125

Lys Leu His Gly Pro Asp Met Gly Gly Thr Val Val Leu Ile His Lys
       130                 135                 140

Ala Gly Thr
145
```

<210> SEQ ID NO 33
<211> LENGTH: 524
<212> TYPE: DNA
<213> ORGANISM: Glycine max
<220> FEATURE:
<221> NAME/KEY: unsure
<222> LOCATION: (386)
<223> OTHER INFORMATION: n = A, C, G or T
<220> FEATURE:
<221> NAME/KEY: unsure
<222> LOCATION: (423)
<223> OTHER INFORMATION: n = A, C, G or T
<220> FEATURE:
<221> NAME/KEY: unsure
<222> LOCATION: (459)
<223> OTHER INFORMATION: n = A, C, G or T
<220> FEATURE:
<221> NAME/KEY: unsure
<222> LOCATION: (481)
<223> OTHER INFORMATION: n = A, C, G or T
<220> FEATURE:
<221> NAME/KEY: unsure
<222> LOCATION: (483)
<223> OTHER INFORMATION: n = A, C, G or T
<220> FEATURE:
<221> NAME/KEY: unsure
<222> LOCATION: (486)
<223> OTHER INFORMATION: n = A, C, G or T

<400> SEQUENCE: 33

```
aaatggcgct gttgtgtggc ggcatgccat ggtcgaaggt gatagttcct cccatttttcc     60
```

-continued

| | |
|---|---|
| accactctca caccctcgc accttcttct tccaacgacg ccgtttctca gtctctgctc | 120 |
| tctccgaaca accaccaccc gttcgcgttc gtttcgctcc ttctcccacc ggaaacctcc | 180 |
| acgtcggcgg tgcccgaacg gccctcttca actacttgtt cgcaaggtcc aaagtggga | 240 |
| aatttgtgct gagaattgag gacactgact tggagaggtc caagtaggga gtctgaggag | 300 |
| gccatgctca aagatctttc ttggcttgga cttgattggg atgaagggcc tgggtgttgg | 360 |
| agggattat ggtccttaaa aggcantctg agaaggaatt ccttatacaa acaatatgcc | 420 |
| ggngaaacta cacaaatccg ggcaagttta accgctgcnt tctggtccaa agagggaact | 480 |
| nanagnaaat gaaaggaggt tgctaaacta agcaactgg cccc | 524 |

<210> SEQ ID NO 34
<211> LENGTH: 94
<212> TYPE: PRT
<213> ORGANISM: Glycine max
<220> FEATURE:
<221> NAME/KEY: UNSURE
<222> LOCATION: (63)
<223> OTHER INFORMATION: Xaa = ANY AMINO ACID

<400> SEQUENCE: 34

Gln Arg Arg Arg Phe Ser Val Ser Ala Leu Ser Glu Gln Pro Pro Pro
1               5                   10                  15

Val Arg Val Arg Phe Ala Pro Ser Pro Thr Gly Asn Leu His Val Gly
            20                  25                  30

Gly Ala Arg Thr Ala Leu Phe Asn Tyr Leu Phe Ala Arg Ser Lys Gly
        35                  40                  45

Gly Lys Phe Val Leu Arg Ile Glu Asp Thr Asp Leu Glu Arg Xaa Ser
    50                  55                  60

Arg Glu Ser Glu Glu Ala Met Leu Lys Asp Leu Ser Trp Leu Gly Leu
65                  70                  75                  80

Asp Trp Asp Lys Gly Leu Gly Val Gly Gly Asp Tyr Gly Pro
            85                  90

<210> SEQ ID NO 35
<211> LENGTH: 506
<212> TYPE: DNA
<213> ORGANISM: Glycine max
<220> FEATURE:
<221> NAME/KEY: unsure
<222> LOCATION: (18)
<223> OTHER INFORMATION: n = A, C, G or T
<220> FEATURE:
<221> NAME/KEY: unsure
<222> LOCATION: (483)
<223> OTHER INFORMATION: n = A, C, G or T
<220> FEATURE:
<221> NAME/KEY: unsure
<222> LOCATION: (505)
<223> OTHER INFORMATION: n = A, C, G or T
<220> FEATURE:
<221> NAME/KEY: unsure
<222> LOCATION: (506)
<223> OTHER INFORMATION: n = A, C, G or T

<400> SEQUENCE: 35

| | |
|---|---|
| ggaacatgga tattattngt gttcccgggg ttatggctga agcagagctt atagcttcta | 60 |
| tcgtcacttt gtttaagcga ataggaatta cagaatcaga tgtcggattt aaggtttcca | 120 |
| gtcgaaaggt tctgcaagaa gtattaaatt gttattcagt accagaaaat ttatttggca | 180 |
| aggtctgcgt cattattgat aaaattgaga aaattccagc tgacgagata aagaaagagt | 240 |
| tgaaagctgt tggtctatct caagaggctg tccaggagct attgcaagtc ctttctgtga | 300 |

-continued

```
agtcattgac cgagttagaa gagagacttg ggagagtggg gaagcagttg ctgatctgaa     360
acagtattct cccttgctga aaaaattggt tactctaaat ggttcaattt gatgatagtt     420
gttcgaggtc ttgcttacta cactggcatt gatttgaggg tttgacgaga ggaagctgca     480
gcntctgtgt gtgtcaatac attgnn                                          506
```

<210> SEQ ID NO 36
<211> LENGTH: 48
<212> TYPE: PRT
<213> ORGANISM: Glycine max

<400> SEQUENCE: 36

Asp Val Gly Phe Lys Val Ser Ser Arg Lys Val Leu Gln Glu Val Leu
 1               5                  10                  15

Asn Cys Tyr Ser Val Pro Glu Asn Leu Phe Gly Lys Val Cys Val Ile
            20                  25                  30

Ile Asp Lys Ile Glu Lys Ile Pro Ala Asp Glu Ile Lys Lys Glu Leu
        35                  40                  45

<210> SEQ ID NO 37
<211> LENGTH: 577
<212> TYPE: DNA
<213> ORGANISM: Triticum sp.
<220> FEATURE:
<221> NAME/KEY: unsure
<222> LOCATION: (140)
<223> OTHER INFORMATION: n = A, C, G or T
<220> FEATURE:
<221> NAME/KEY: unsure
<222> LOCATION: (370)
<223> OTHER INFORMATION: n = A, C, G or T
<220> FEATURE:
<221> NAME/KEY: unsure
<222> LOCATION: (411)
<223> OTHER INFORMATION: n = A, C, G or T
<220> FEATURE:
<221> NAME/KEY: unsure
<222> LOCATION: (413)
<223> OTHER INFORMATION: n = A, C, G or T
<220> FEATURE:
<221> NAME/KEY: unsure
<222> LOCATION: (469)
<223> OTHER INFORMATION: n = A, C, G or T
<220> FEATURE:
<221> NAME/KEY: unsure
<222> LOCATION: (481)
<223> OTHER INFORMATION: n = A, C, G or T
<220> FEATURE:
<221> NAME/KEY: unsure
<222> LOCATION: (504)
<223> OTHER INFORMATION: n = A, C, G or T
<220> FEATURE:
<221> NAME/KEY: unsure
<222> LOCATION: (575)
<223> OTHER INFORMATION: n = A, C, G or T
<220> FEATURE:
<221> NAME/KEY: unsure
<222> LOCATION: (530)
<223> OTHER INFORMATION: n = A, C, G or T
<220> FEATURE:
<221> NAME/KEY: unsure
<222> LOCATION: (551)
<223> OTHER INFORMATION: n = A, C, G or T
<220> FEATURE:
<221> NAME/KEY: unsure
<222> LOCATION: (556)
<223> OTHER INFORMATION: n = A, C, G or T
<220> FEATURE:
<221> NAME/KEY: unsure
<222> LOCATION: (564)
<223> OTHER INFORMATION: n = A, C, G or T

<400> SEQUENCE: 37

```
cttgggatta catcttctga tgtggggatc agactgtcca gccgaaaggt tctacaggcc      60
gtgttggata tgtactccgt accacaacac ttgtttactc aagtttgtgt tattgttgac     120
aagctgggga aactgagtan ggaagaaatt gagaaggaat tgatttcaac tgggctgtca    180
tctgaagcag tacagggcat cattgaagtg ctctctctca agtcactgtc caaacttgaa    240
gaggtgctag gctcaggtgt tgaagccgtt gctgacttga agaacctctt ctcgcttgct    300
gagcaatatg gttattctga ttggatctgt ttcgatgcat ctgttgttcg tggccttgca    360
tactacacan gggattgttt ttgaggcttt tgatagggaa gggaaactga nancatttgt    420
ggtgggggg aggtatgaca ggctacgtca acatttggaa ctgaagatnt ccaccctgtg     480
nctttggatt tggaatcctg tcanagtgga ctccnaaaga aaggtctttn ctacctgcac    540
tcaaataata nattgntcca ttgncaagac ttggggg                              577
```

<210> SEQ ID NO 38
<211> LENGTH: 46
<212> TYPE: PRT
<213> ORGANISM: Triticum sp.
<220> FEATURE:
<221> NAME/KEY: UNSURE
<222> LOCATION: (38)
<223> OTHER INFORMATION: Xaa = ANY AMINO ACID

<400> SEQUENCE: 38

```
Ile Arg Leu Ser Ser Arg Lys Val Leu Gln Ala Val Leu Asp Met Tyr
  1               5                  10                  15

Ser Val Pro Gln His Leu Phe Thr Gln Val Cys Val Ile Val Asp Lys
                 20                  25                  30

Leu Gly Lys Leu Ser Xaa Glu Glu Ile Glu Lys Glu Leu Ile
             35                  40                  45
```